United States Patent
Mulqueeny et al.

(10) Patent No.: US 9,392,964 B2
(45) Date of Patent: Jul. 19, 2016

(54) DETECTION OF ASYNCHRONY

(75) Inventors: Qestra Camille Mulqueeny, Mosman (AU); Stephen James Redmond, Coogee (AU); Nigel Hamilton Lovell, Coogee (AU)

(73) Assignee: ResMed Limited (AU)

( * ) Notice: Subject to any disclaimer, the term of this patent is extended or adjusted under 35 U.S.C. 154(b) by 1232 days.

(21) Appl. No.: 13/264,012

(22) PCT Filed: Apr. 22, 2010

(86) PCT No.: PCT/AU2010/000457
§ 371 (c)(1),
(2), (4) Date: Oct. 12, 2011

(87) PCT Pub. No.: WO2010/121313
PCT Pub. Date: Oct. 28, 2010

(65) Prior Publication Data
US 2012/0037159 A1 Feb. 16, 2012

Related U.S. Application Data

(60) Provisional application No. 61/171,606, filed on Apr. 22, 2009.

(51) Int. Cl.
*A61B 5/087* (2006.01)
*A61B 5/091* (2006.01)
(Continued)

(52) U.S. Cl.
CPC ............... *A61B 5/087* (2013.01); *A61B 5/085* (2013.01); *A61B 5/091* (2013.01);
(Continued)

(58) Field of Classification Search
CPC ............... A61M 16/0051; A61M 2016/0027; A61M 2016/0036; A61M 2205/502; A61M 2205/52; A61M 2230/42; A61M 2230/65; A61B 5/085; A61B 5/087; A61B 5/091; A61B 5/7264
See application file for complete search history.

(56) References Cited

U.S. PATENT DOCUMENTS 4,351,344 A  9/1982 Stenzler
4,448,192 A  5/1984 Stawitcke et al.
(Continued)

FOREIGN PATENT DOCUMENTS

EP  1346743 A1  9/2003
GB  2077444 A  12/1981
(Continued)

OTHER PUBLICATIONS

Thille, Arnaud, et al. "Patient-ventilator asynchrony during assisted mechanical ventilation," Intensive Care Med (2006) 32:1515-1522.*
(Continued)

*Primary Examiner* — Justine Yu
*Assistant Examiner* — Timothy Stanis
(74) *Attorney, Agent, or Firm* — Lerner, David, Littenberg, Krumholz & Mentlik, LLP

(57) ABSTRACT

A controller or processor(s) (1112) implements detection of respiratory related conditions, such as asynchrony, associated with use of a respiratory treatment apparatus (1102) or ventilator. Based on data derived from sensor signals associated with the respiratory treatment, the detector may evaluate a feature set of detection values to determine whether or not an asynchrony occurs in a breath of the patient's respiratory cycle such as by comparing the values against a set of thresholds. Different events may also be identified based on the particular feature set and threshold(s) involved in the detection processing. Automated determination of feature sets may also be implemented to design different asynchrony event classifiers. The methodologies may be implemented by computers or by respiratory treatment apparatus. The detection of such asynchrony events can then also serve as part of control logic for automated adjustments to the control parameters of the respiratory treatment generated by the respiratory treatment apparatus.

39 Claims, 19 Drawing Sheets

(51) Int. Cl.
   *A61B 5/085* (2006.01)
   *A61M 16/00* (2006.01)
   *A61B 5/00* (2006.01)

(52) U.S. Cl.
   CPC ......... *A61M 16/0051* (2013.01); *A61B 5/7264* (2013.01); *A61M 2016/0027* (2013.01); *A61M 2016/0036* (2013.01); *A61M 2205/502* (2013.01); *A61M 2205/52* (2013.01); *A61M 2210/1014* (2013.01); *A61M 2230/42* (2013.01); *A61M 2230/65* (2013.01)

(56) References Cited

U.S. PATENT DOCUMENTS

| | | | |
|---|---|---|---|
| 4,844,085 | A | 7/1989 | Gattinoni |
| 6,213,119 | B1 | 4/2001 | Brydon et al. |
| 6,305,374 | B1* | 10/2001 | Zdrojkowski et al. ... 128/204.21 |
| 6,439,229 | B1 | 8/2002 | Du et al. |
| 6,626,175 | B2 | 9/2003 | Jafari et al. |
| 2003/0050568 | A1* | 3/2003 | Green et al. ................. 600/538 |
| 2003/0196663 | A1 | 10/2003 | Wenkebach et al. |
| 2004/0050387 | A1 | 3/2004 | Younes |
| 2005/0087190 | A1 | 4/2005 | Jafari et al. |
| 2008/0110461 | A1* | 5/2008 | Mulqueeny et al. ..... 128/204.23 |
| 2009/0301486 | A1* | 12/2009 | Masic ...................... 128/204.21 |
| 2010/0016694 | A1* | 1/2010 | Martin et al. ................. 600/324 |
| 2012/0073574 | A1* | 3/2012 | Gutierrez ................. 128/204.18 |

FOREIGN PATENT DOCUMENTS

| | | |
|---|---|---|
| JP | 57022744 | 2/1982 |
| JP | 57-501717 | 9/1982 |
| JP | 58-159762 | 9/1983 |
| JP | 62-90136 | 4/1987 |
| JP | 03-222963 | 10/1991 |
| JP | 2004512065 A | 4/2004 |
| JP | 2008516702 A | 5/2008 |
| WO | 0228460 A1 | 4/2002 |
| WO | 2004002561 A2 | 1/2004 |
| WO | 2005/063323 A1 | 7/2005 |
| WO | 2006079152 A1 | 8/2006 |
| WO | 2008025064 A1 | 3/2008 |
| WO | 2008131798 A1 | 11/2008 |

OTHER PUBLICATIONS

International Search Report and Written Opinion, PCT/AU2010/000457, dated Aug. 20, 2010.

Georgopoulos D. et al., "Bedside Waveforms Interpretation as a Tool to Identify Patient-Ventilator Asynchronies", Intensive Care Med (2006) 32: 34-37.

Mulqueeny Q. et al "Aulomatic Detection of Ineffective Triggering and Double Triggering During Mechanical Ventilalion", Intensive Care Med (2007) 33: 2014-2018.

Yamada Y. et al., "Analysis of the Mechanisms of Expiralory Asynchrony in pressure Support Ventilation: A Mathematical Approach", J Appl Physiol (2000) 88: 2143-2150.

Mulqueeny Q. et al., "Automated Detection of Asynchrony in Patient-Ventilator Interaction", 31st Anuual International Conference of the IEEE EMBS, Sep. 2-6 2009.

Chen C.W, et al., "Detecting Ineffective Triggering in the Expiratory Phase in Mechanical Ventilated Patients Based on Airway Flow and Pressure Deflections; Feasibility of Using a Computer Algorithm", Crit Care Med (2008) vol. 36, No. 2 See pp. 456-458.

Japanese Office Action for Application No. JP2012-506280 dated Feb. 28, 2014.

\* cited by examiner

DETECTION OF ASYNCHRONY

CROSS REFERENCE TO RELATED APPLICATIONS

This application claims the benefit of the filing date of U.S. Provisional Patent Application No. 61/171,606 filed Apr. 22, 2009, the disclosure of which is hereby incorporated herein by reference.

FIELD OF THE TECHNOLOGY

The present technology relates to methods and apparatus for the detection of respiratory treatment related conditions or events such as the conditions indicative of asynchrony.

BACKGROUND OF THE TECHNOLOGY

Ensuring quality interaction between a patient and their respiratory treatment apparatus can be significant. For example, quality interaction between a patient and their ventilator is critical to minimize the work of breathing of the patient. Increased work of breathing caused by patient-ventilator asynchrony is associated with negative patient outcomes and has been shown to be highly prevalent; studies have shown up to 47% of ventilator delivered breaths may be asynchronous.

With proper supervision and adjustment of ventilator settings, asynchrony may be manually mitigated by the clinician. However, monitoring asynchrony is a challenge. Knowledge of its existence may require high resolution and real-time display of airway pressure delivered by the ventilator, the patient's airflow and a measure of inspiratory activity, such as diaphragmatic EMG or esophageal pressure measured invasively via a balloon catheter. Furthermore, expert visual interpretation of these signals can be critical to diagnose the quality of patient-ventilator interaction.

It may be desirable to develop further methods and devices for automating detection of asynchrony that may improve respiratory treatment apparatus.

SUMMARY OF THE TECHNOLOGY

Aspects of the present technology involve methods and apparatus for a detection of asynchrony.

Still further aspects of the technology involve methods and apparatus for development of devices for detection of asynchrony.

In one such example embodiment, an automated processing method is provided for detection of asynchrony of a respiratory treatment apparatus that controls a delivery of a synchronized respiratory treatment. The method may include determining detection values of a feature set with data derived from signals of at least one sensor coupled with the respiratory treatment apparatus. The method may further include comparing with a processor the feature set of detection values with a set of stored data thresholds. The method may also include determining with the processor an occurrence of an asynchrony event between the respiratory treatment apparatus and a patient respiratory cycle based on the comparison.

In another embodiment, an apparatus for detection of asynchrony between a synchronized respiratory treatment and a respiratory cycle is provided. The apparatus may include a memory containing data representing a feature set of detection values derived from signals of at least one sensor coupled with the respiratory treatment apparatus. The apparatus may also include a processor to access the data. The processor may be configured to control a comparison of the data of the feature set of detection values with a set of stored data thresholds of the memory. It may also be configured to control a determination of an occurrence of an asynchrony event between the respiratory treatment apparatus and a patient respiratory cycle based on the comparison. In addition, it may be configured to control a generation of an output representing the occurrence of the asynchrony event.

In some embodiments, the feature set of detection values may include any one or more of a respiratory rate based feature, a respiratory volume based feature, a respiratory mechanics based feature, an expiratory flow morphology based feature.

In some embodiments, the apparatus or method may also determine or identify a plurality of distinct asynchrony events based on the comparison. The asynchrony events may be any one or more of an expiratory ineffective effort event, a post-triggering effort event, a double triggering event, an autotriggering event, a late triggering event, an early cycling event, a late cycling event, and/or an inspiratory ineffective effort event.

In an example embodiment, the feature set of detection values for detecting an inspiratory ineffective effort event may include (a) power of a piecewise bilinear approximation of a remainder of expiration after a location of a maximum expiratory flow, (b) a distance between a maximum and minimum values of a moving average expiratory flow, (c) an integral of a rectified and de-trended moving average of expiratory flow, (d) an inspiratory time constant (e) and a fraction of said distance and a peak expiratory flow.

In some embodiments, the processor may be or be part of a controller of the respiratory treatment apparatus, which may be a ventilator, and the sensor may be a flow sensor. The controller may then be configured to detect a respiratory cycle with the signal of the flow sensor and to generate flow generator control signals for producing the respiratory treatment.

In some embodiments of the method or apparatus, the feature set are selected by a selecting process such that the feature set comprises a subset of a superset of features. Such a selecting process may include evaluating, with a processor, values of the superset for known asynchronous events occurring in data of a plurality of breaths established with a plurality of respiratory treatment apparatus. The evaluating process may involve calculating posterior-probabilities with values of the superset by Parzen-window estimation, wherein groups of values of the superset are selected by iteratively including and removing values. The evaluation may also include detecting asynchrony events with the selected subset of features and comparing the events detected with known events data to test or assess the performance of the subset.

In some embodiments, the apparatus may include a patient interface to carry a flow of breathable gas to a patient. It may also include a flow generator coupled with the patient interface to generate a flow of the breathable gas through the patient interface. The apparatus may also include a transducer, such as a pressure transducer or differential pressure transducer. The transducer may provide a signal indicative of patient flow through the patient interface. The processor may serve as a controller of the flow generator so that the controller is configured to detect a respiratory cycle with the signal of the flow sensor and to generate flow generator control signals for producing the respiratory treatment.

In some embodiments, a system is provided for detection of asynchrony between a synchronized respiratory treatment and a respiratory cycle. The system may include a processing means for processing data derived from one or more pressure transducer signals from use of respiratory treatment apparatus. The processing means may be configured for (a) comparing a feature set of detection values calculated from the data with a set of stored data thresholds, and (b) determining an occurrence of an asynchrony event between the respiratory treatment apparatus and a patient respiratory cycle based on the comparison. The system may also include classification means for selecting the feature set such that the feature set comprises a subset of a superset of features, wherein the selecting comprises evaluating values of the superset for known asynchronous events occurring in data of a plurality of breaths established with a plurality of respiratory treatment apparatus. The processing means of the system may also be configured for calculating the detection values of the feature set with the data derived from signals of at least one sensor.

In some embodiments of such a system, the feature set of detection values may be two or more of features of a group of features consisting of (a) a respiratory rate based feature; (b) a respiratory volume based feature; (b) a respiratory mechanics based feature; (d) an expiratory flow morphology based feature.

In further embodiments of such a system, the occurrence of the asynchrony event may be an asynchrony event of a group of asynchrony events consisting of (a) an expiratory ineffective effort event, (b) a post-triggering effort event, (c) a double triggering event, (d) an autotriggering event (e) a late triggering event, (f) an early cycling event, and (g) a late cycling event.

The system may also include an interface means to carry a flow of breathable gas, a flow generation means, coupled with the interface means, for generating the breathable gas, and a flow sensor for generating the pressure transducer signals. In such a system, the processing means may be further configured for controlling the flow generation means to provide a synchronized respiratory treatment, such as respiratory support ventilation.

In some embodiments, the methodologies may be contained on information bearing medium such as a memory. For example, an information-bearing medium may have processor-readable information thereon. The processor-readable information may control an apparatus for detection of asynchrony between a synchronized respiratory treatment and a respiratory cycle. The processor-readable information may then include control instructions to access detection values of a feature set with data derived from signals of at least one sensor coupled with the respiratory treatment apparatus, to compare the feature set of detection values with a set of stored data thresholds, and to determine an occurrence of an asynchrony event between the respiratory treatment apparatus and a patient respiratory cycle based on the comparison.

In some embodiments of the present technology, a respiratory treatment apparatus estimates respiratory resistance and compliance based on measures of flow and pressure. The apparatus may include one or more sensors to generate signals representative of flow and pressure. The apparatus may also include a processor, coupled with the one or more sensors. The processor may be configured to control detecting a portion of expiration of a breathing cycle from data of the flow signal. It may also be configured to control calculating a resistance value and compliance value with flow, pressure and volume measures that correspond to the detected portion of expiration.

In some embodiments, the detected portion of expiration may a portion that begins at an expiration cycle and ends when an expired tidal volume for the expiration cycle exceeds a limit in a range of about 85 to 90 percent. The compliance and resistance values may optionally be calculated by a multiple linear regression process with data representing the flow, pressure and volume measures. Moreover, this may be calculated in a breath by breath process. The processor may be further configured to control an assessment of accuracy of the determined resistance and compliance values. The assessment of accuracy may involve calculating a coefficient of determination and comparing it to a threshold.

In some embodiment, the processor of the respiratory treatment apparatus may be further configured to control determining a PEEP control parameter based on a plurality of compliance values determined by the processor. In such a process, the processor may control a repeated change, such as a step reduction, to a preset PEEP control parameter during which a plurality of pressure and flow measures are determined. The plurality of compliance values may then be determined based on the plurality of pressure and flow measures. This determination may involve detecting an inflection point from data representing the plurality of compliance values.

In some embodiments, the processor of the respiratory treatment apparatus may also be configured to control determining a maximum pressure support limit based on a plurality of determined compliance values. In such a process, the processor may controls a repeated change, such as a stepped reduction, to a preset PEEP control parameter during which a plurality of pressure and flow measures are determined. The processor then may determine the plurality of compliance values based on the plurality of pressure and flow measures. Optionally, the determining of the maximum pressure support limit may involve detecting an inflection point from data representing the plurality of compliance values. In some such embodiments, the respiratory treatment apparatus may also include a flow generator, coupled with the processor, to generate a flow of breathable gas at pressures above atmospheric to a patient interface based on control signals from the processor.

Further embodiments and features of the technology will be apparent from the following detailed disclosure, claims and drawings.

BRIEF DESCRIPTION OF THE DRAWINGS

The present technology is illustrated by way of example, and not by way of limitation, in the figures of the accompanying drawings, in which like reference numerals refer to similar elements including.

DETAILED DESCRIPTION

The present technology involves automated detection of asynchrony events related to the delivery of respiratory treatment. Asynchrony involves situations when the actual state of the patient's respiration is not in phase with an automated respiratory treatment that is intended to be synchronized with the patient's respiration. As previously mentioned, asynchrony can occur in patient-ventilator interaction. The current technology may be employed to develop or implement asynchrony detectors. Such detectors may serve to determine whether or not one or more asynchrony events has or is occurring. The detectors may also be implemented for identification or classification of one or more different types of asynchrony events.

Figure 1:
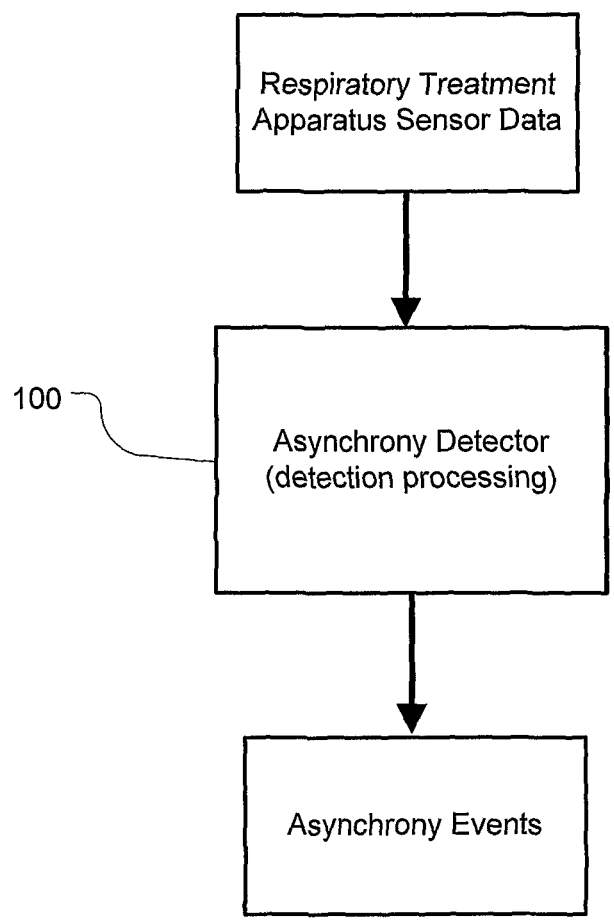
FIG. 1 is an block diagram of an example asynchrony detector of the present technology.

An asynchrony detection embodiment is illustrated in FIG. 1. Typically, asynchrony detector 100, such as a programmed processor, may access data or signals from one or more sensors associated with a respiratory treatment apparatus that provides a synchronized respiratory treatment. For example, the data may be based on flow f(t) and/or pressure p(t) signals taken from a flow sensor and/or pressure sensor of such an apparatus. Based on this data the detector 100 may then detect or identify asynchrony events.

Figure 2:
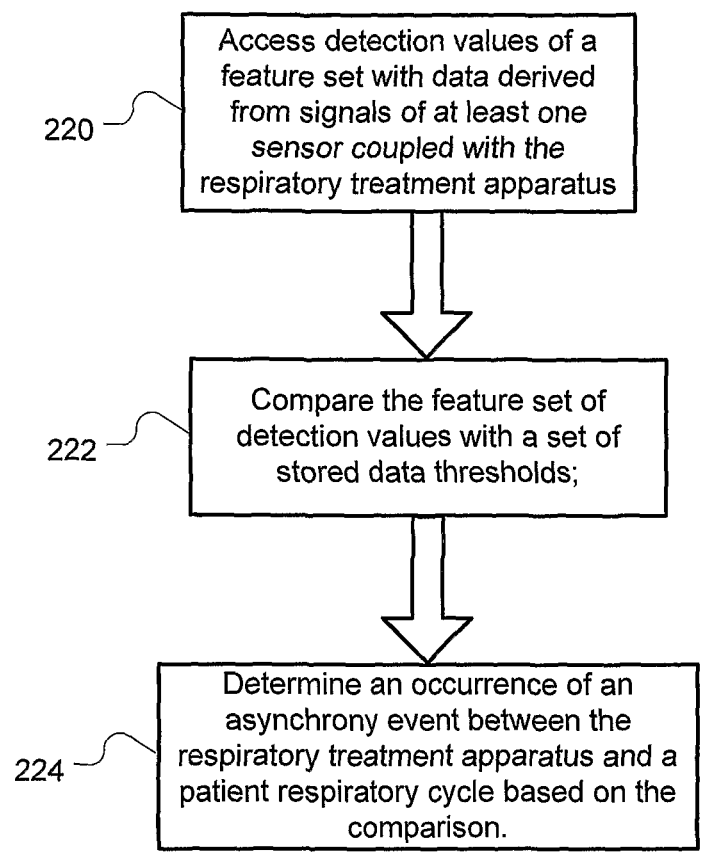
FIG. 2 is an flow chart with an example methodology that may be implemented in some embodiments of the asynchrony detector of FIG. 1.

For example, in some embodiments the detector may implement a methodology illustrated in the flow chart of FIG. 2. At 220, a processor may access detection values of a feature set with data derived from signals of at least one sensor coupled with the respiratory treatment apparatus. The processor may then evaluate the detection values. For example, at 222, the processor may then compare the feature set of detection values with a set of stored data thresholds. At 224, the processor may determine an occurrence of an asynchrony event between the respiratory treatment apparatus and a patient respiratory cycle based on the evaluation or comparison.

Information of the detected events may be recorded in the memory of a device and/or output to a display apparatus. Similarly, it may be transmitted (e.g., via wired or wireless communication) for review or analysis with other processing apparatus. The stored or recorded data representing information of the events may, for example, include an identification of event type, time of occurrence, count of all asynchrony events for a period of use, count of each type of detected event for a period of use, etc. Other data of the sensors of the apparatus may be associated with the asynchrony event(s) and may also be stored for further analysis in conjunction with the asynchrony event information. For example, the flow and/or pressure signals data for each patient breathing cycle identified as asynchronous may also be stored.

In some embodiments, asynchrony events may be scored and output by the processor. The score may be used as a performance index for a particular respiratory treatment apparatus or treatment session with the apparatus. For example, the score may be represented as a ratio of a number of asynchrony events per time period (e.g., a treatment period) or per ventilator breaths delivered.

The processor may also be configured to analyze the scored events to implement or suggest changes to the treatment control of the respiratory treatment apparatus. For example, as discussed in more detail herein, detected asynchrony events may serve as part of the processing control logic to automatically change certain control parameters of a pressure treatment delivered by a respiratory treatment apparatus. Similarly, detected asynchrony events may serve as part of the processing control logic to automatically output messages to suggest that manual changes to certain control parameters of a pressure treatment delivered by a respiratory treatment apparatus be changed.

Example Detectable Asynchrony Events

The asynchrony detector 100 in some embodiments may be configured to detect any one or more of the different types of asynchrony events graphically illustrated in FIGS. 3-9. As further discussed herein, the illustrated events may be considered expiratory ineffective effort events, post-triggering effort events, double triggering events, autotriggering events, late triggering events, early cycling events, late cycling events and/or inspiratory ineffective effort events.

Figure 3:
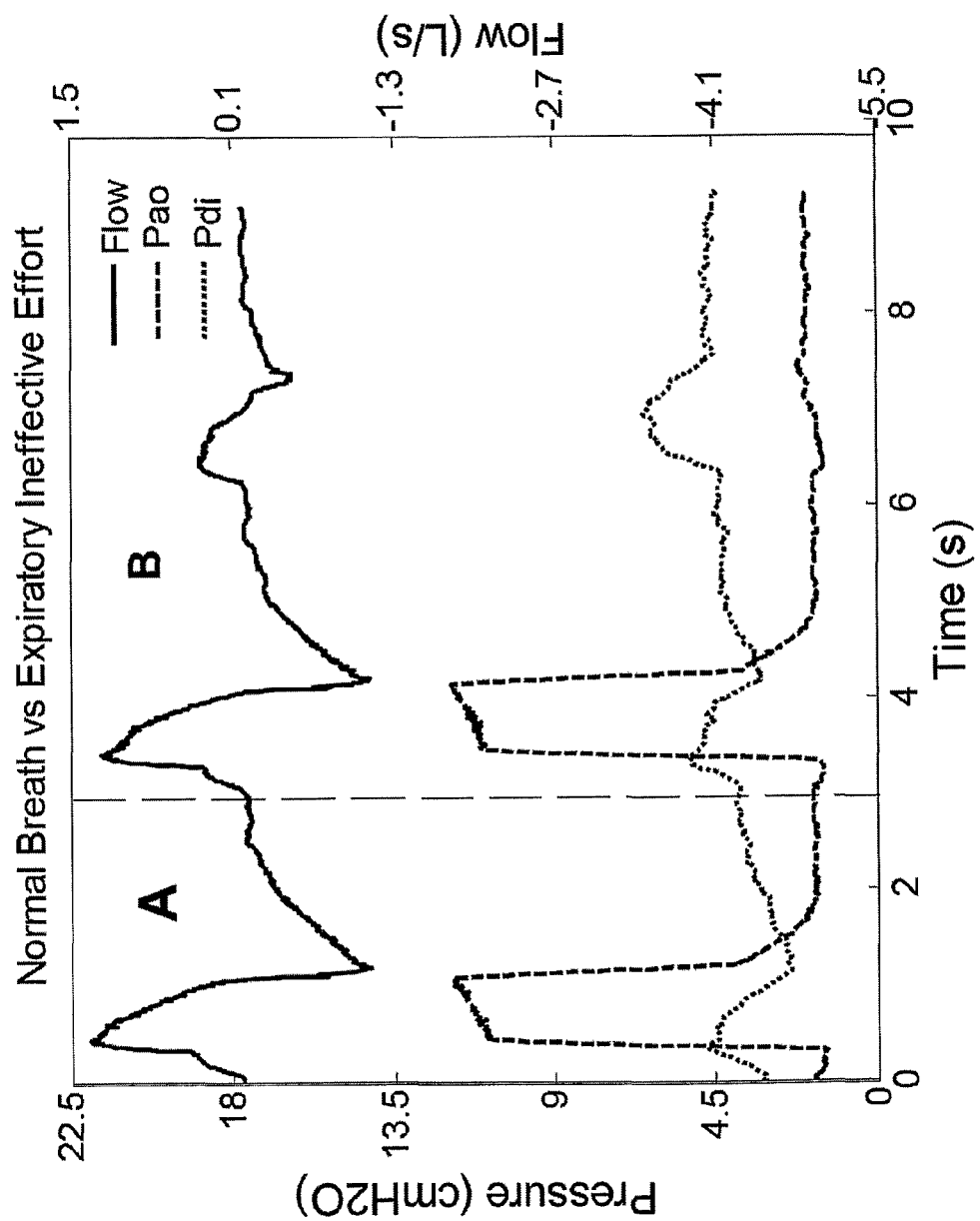
FIG. 3 is a graph illustrating flow, pressure and transdiaphragmatic pressure corresponding to an expiratory ineffective effort asynchrony event that may be detected with the present asynchrony detection technology.

FIG. 3. is a graphic illustration of an example expiratory ineffective effort event. The graph has a plot of a flow signal, airway pressure ("Pao") signal and transdiaphragmatic pressure ("Pdi") signal during a normal breath in section A and a breath with an expiratory ineffective effort event in section B. A positive swing in the Pdi indicates inspiratory effort by the patient. As illustrated, the breath of section B has a predominant perturbation on the flow signal during mid-expiration. This asynchrony event may also be characterized as a positive Pdi tidal swing during expiration not followed by inspiratory support from a respiratory treatment apparatus or ventilator.

Figure 4:
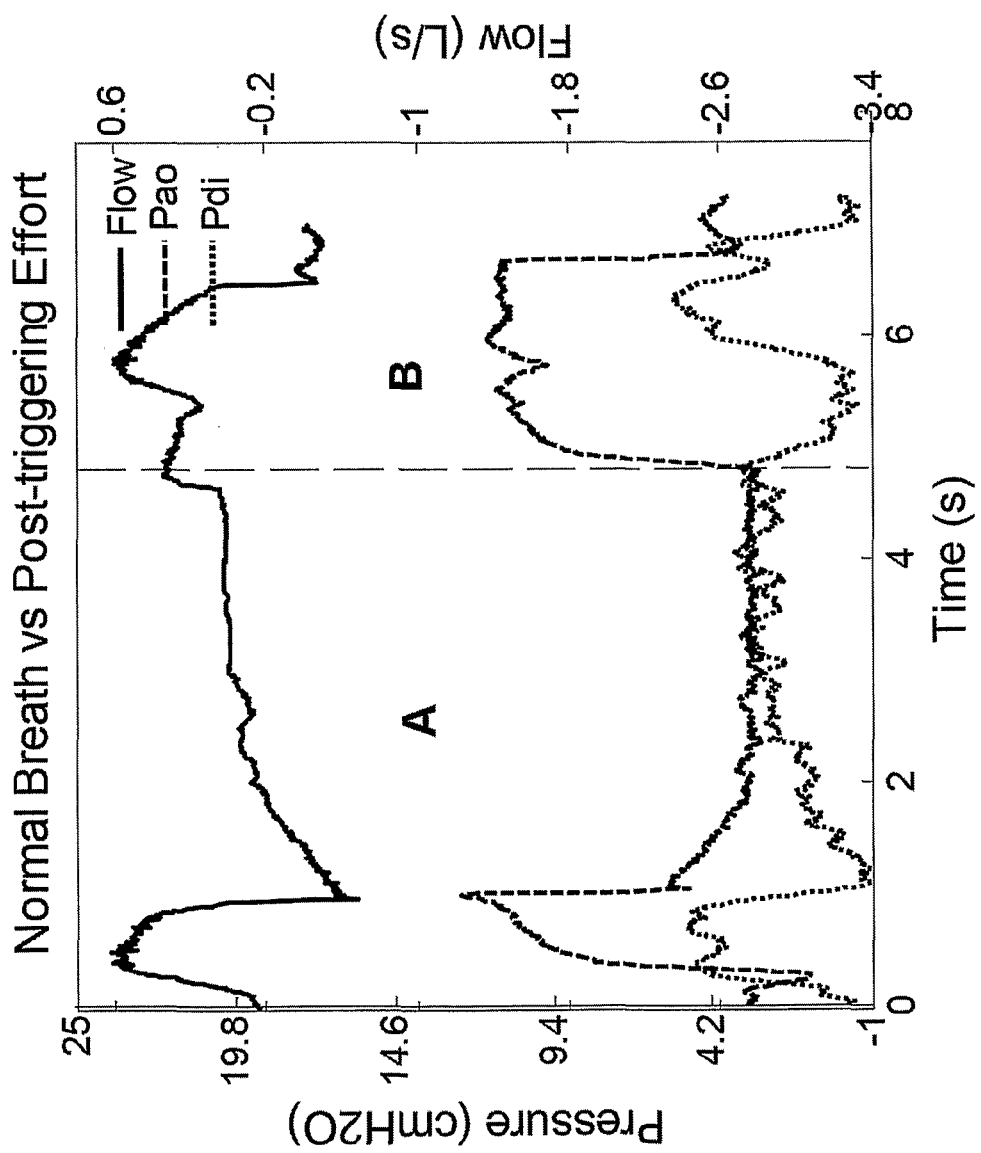
FIG. 4 is a graph illustrating flow, pressure and transdiaphragmatic pressure corresponding to a post-triggering effort asynchrony event that may be detected with the present asynchrony detection technology.

FIG. 4. is a graphic illustration of an example post-triggering effort event. The graph has a plot of a flow signal, airway pressure Pao signal and transdiaphragmatic pressure Pdi signal during a normal breath in section A and a breath with an post-triggering effort event in section B. The graph illustrates a positive Pdi tidal swing beginning after the respiratory treatment apparatus or ventilator has triggered and occurring while the apparatus is delivering inspiratory support that results in an increase in flow. The onset of inspiratory support in section B in this example is machine-triggered.

Figure 5:
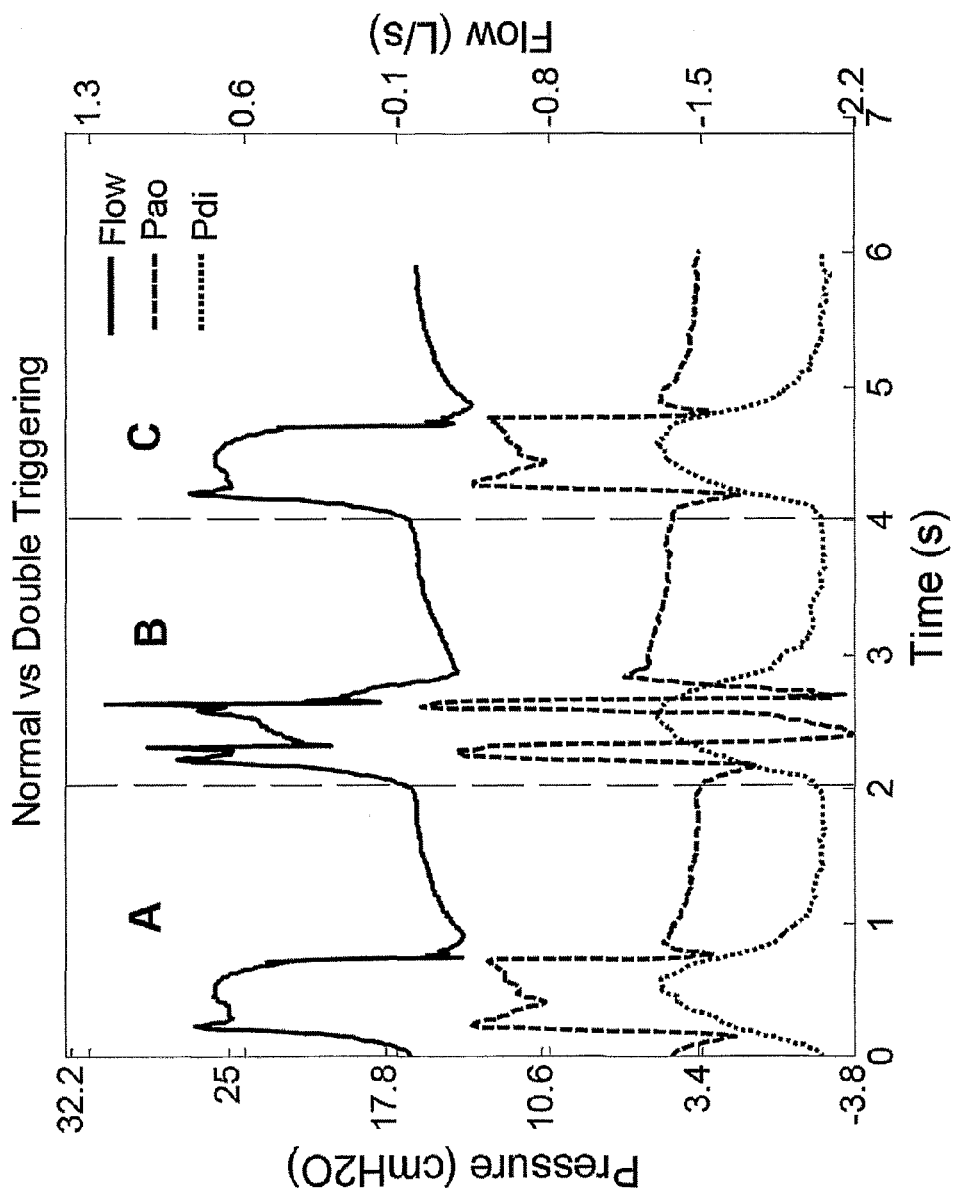
FIG. 5 is a graph illustrating flow, pressure and transdiaphragmatic pressure corresponding to a double triggering asynchrony event that may be detected with the present asynchrony detection technology.

FIG. 5. is a graphic illustration of an example double triggering event. The graph plots a flow signal, airway pressure Pao signal and transdiaphragmatic pressure Pdi signal during two normal breaths in sections A and C and a breath with a double triggering event in section B. Two mechanical breaths over a single Pdi tidal swing are delivered. The first cycle is patient-triggered and separated from the second by a very short expiratory time that may be defined as being less than about one-half of the mean inspiratory time (over 5 mins).

Figure 6:
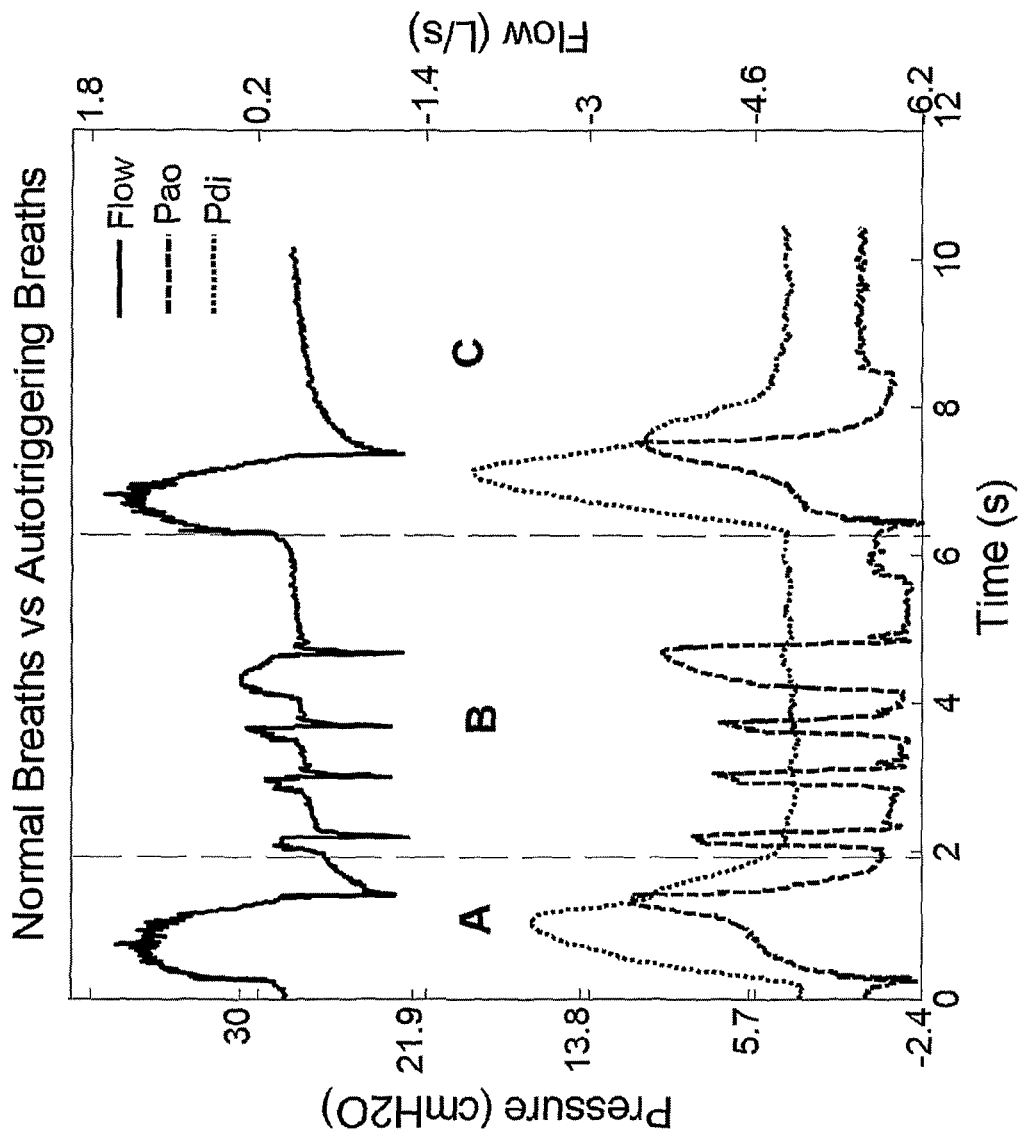
FIG. 6 is a graph illustrating flow, pressure and transdiaphragmatic pressure corresponding to an autotriggering asynchrony event that may be detected with the present asynchrony detection technology.

FIG. 6. is a graphic illustration of an example autotriggering event. The graph plots a flow signal, airway pressure Pao signal and transdiaphragmatic pressure Pdi signal during two normal breaths in section A and C and a sequence of autotriggering events in section B. The event may involve the delivery of inspiratory support by the respiratory treatment apparatus or ventilator without a concomitant swing in Pdi that would otherwise indicate patient effort. This can be taken to indicate that the device delivered a breath that was not triggered by the patient.

Figure 7:
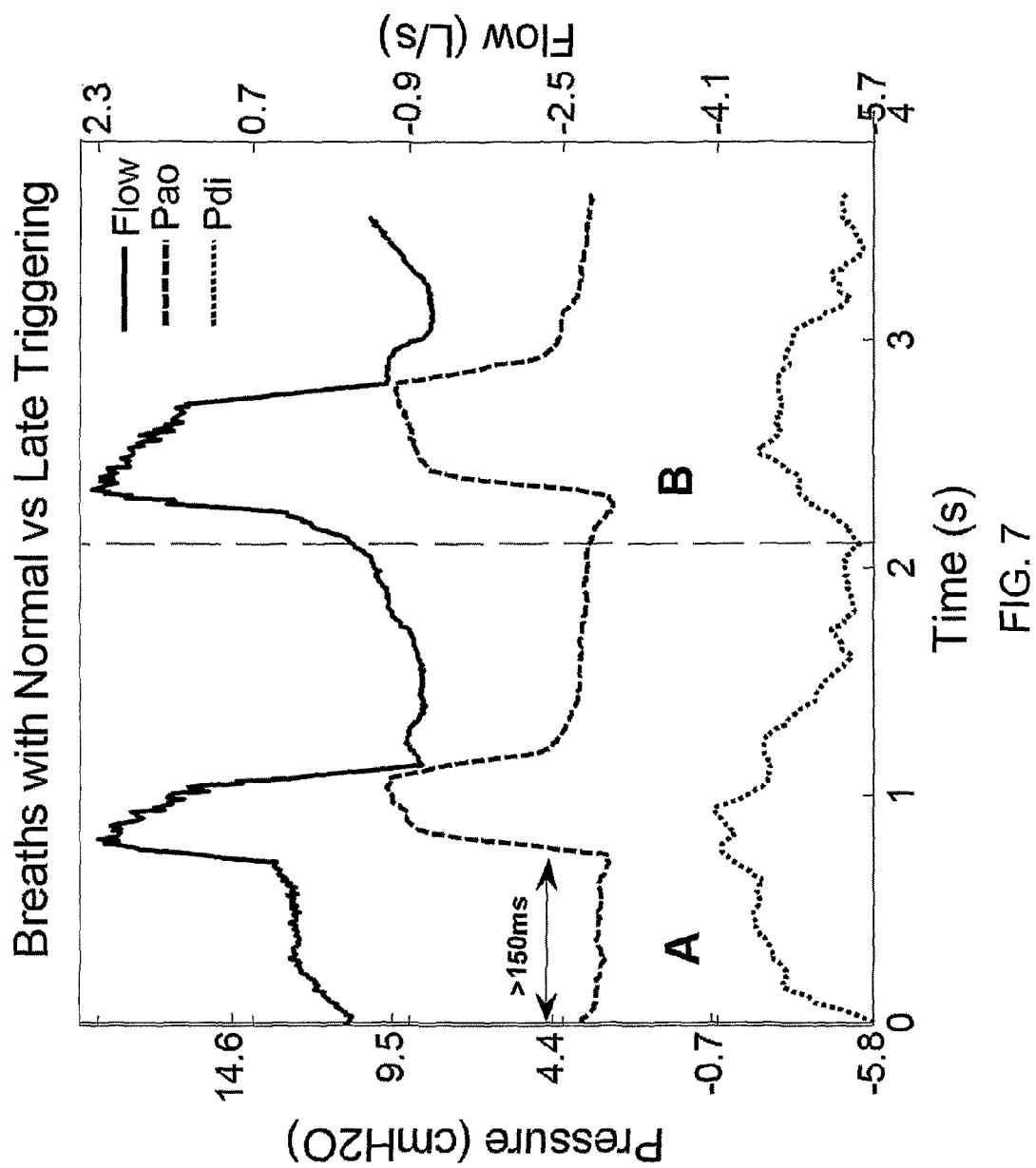
FIG. 7 is a graph illustrating flow, pressure and transdiaphragmatic pressure corresponding to a late triggering asynchrony event that may be detected with the present asynchrony detection technology.

FIG. 7. is a graphic illustration of an example late triggering event. The graph plots a flow signal, airway pressure Pao signal and transdiaphragmatic pressure Pdi signal during a normal breath in section B and a breath with an late triggering event in section A. The graph shows a positive tidal swing in Pdi during expiration that is not followed by inspiratory pressure support from the device until more than 150 ms has elapsed. The increase in Pdi indicates that the start of patient effort was more than 150 ms after the device delivered pressure support.

Figure 8:
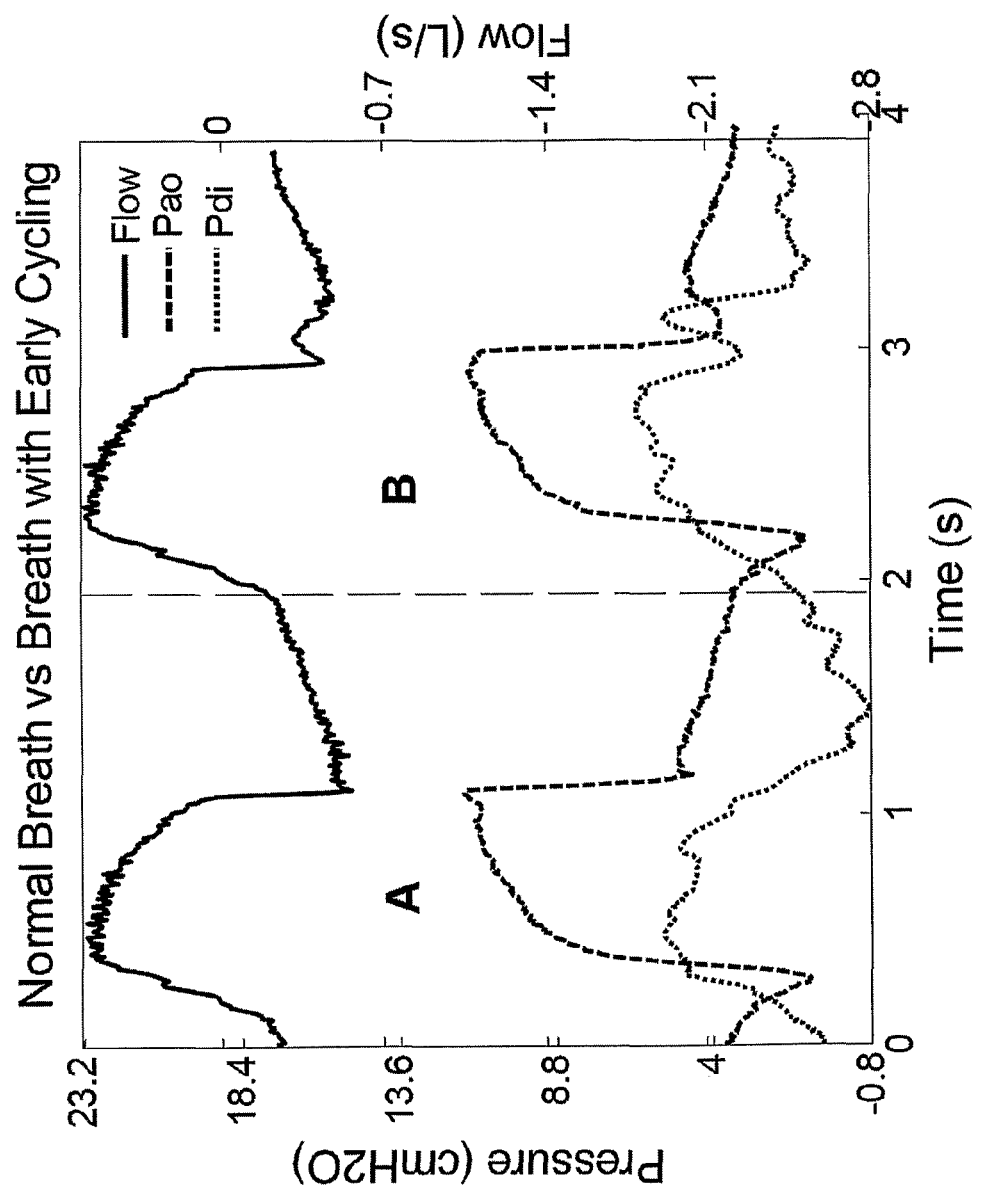
FIG. 8 is a graph illustrating flow, pressure and transdiaphragmatic pressure corresponding to an early cycling asynchrony event that may be detected with the present asynchrony detection technology.

FIG. 8. is a graphic illustration of an example early cycling event. The graph plots a flow signal, airway pressure Pao signal and transdiaphragmatic pressure Pdi signal during a normal breath in section A and a breath with the early cycling event in section B. A cessation or termination of inspiratory support by the device (e.g., advancing to the device's expiratory state) prior to the end of the patient's Pdi tidal swing can indicate that the patient's effort is prolonged beyond the device's mechanical breath.

Figure 9:
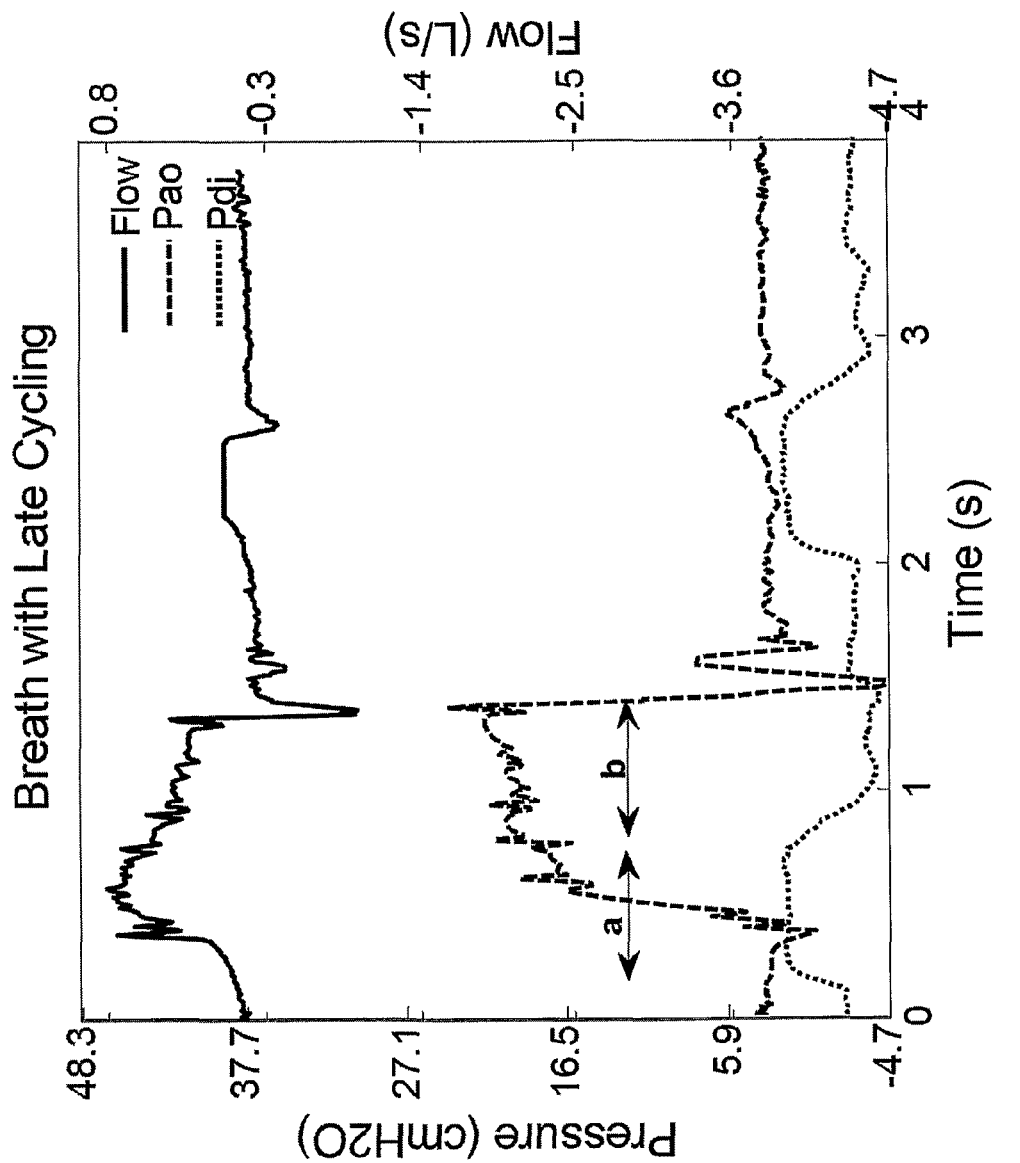
FIG. 9 is a graph illustrating flow, pressure and transdiaphragmatic pressure corresponding to a late cycling asynchrony event and an inspiratory ineffective effort asynchrony event that may be detected with the present asynchrony detection technology.

FIG. 9. is a graphic illustration of an example late cycling event. The graph plots a flow signal, airway pressure Pao signal and transdiaphragmatic pressure Pdi signal during a breath with the late cycling event. The event may be characterized as a prolongation of the device's inspiratory time or inspiratory state that is beyond the end of the patient's inspiratory effort. For example, it may be considered to exist when the time $T_b$ is greater than half of the time $T_a$ (e.g., $T_b > T_a/2$) where:

$T_b$ is the prolongation of the device inspiratory time beyond the end of patient effort; and $T_a$ is the duration of patient inspiratory effort.

FIG. 9 also illustrates an inspiratory ineffective effort event. This event is shown occurring on the time scale between two and three seconds. The graph of this time period shows the transdiaphragmatic pressure Pdi signal increasing and decreasing without a related or corresponding change in the airway pressure Pao signal.

Example Features Sets

As previously mentioned, the detector 100 in some embodiments may be configured to detect the aforementioned different types of asynchrony events based on feature sets of detection values or variables, for example, by detecting a certain pattern or patterns with detection values of one or more feature sets. These sets may include one or more features calculated or determined from the sensor signals that detect information about patient respiration and/or information about the respiratory treatment apparatus. For example, embodiments of the technology may be implemented to utilize, calculate values for or determine the features based on the measurement signals as illustrated in the graphs of FIGS. 3-9. Nevertheless, in still further embodiments, the features may be based on non-invasive measurement signals of a pressure sensor and/or flow sensor rather than an invasive transdiaphragmatic pressure sensor.

Example features of the set of detection values may include, respiratory rate based features, volume based features, respiratory mechanics based features, expiratory flow morphology based features, power based power based features, etc., derivable with pressure and/or flow data. For example, as discussed in more detail herein, such detection variables may be any one or more of the following detection variables: RR breath, RR ratio, IE ratio, $Vol_I$, $Vol_E$, breathLeak, Vol ratio, PEEPii, $R_i$, $C_i$, $Tau_i$, PEEPie, Re, Ce, $Tau_e$, InterpMinima, InterpMinima-⅔, PW linear approx power, PW vol deviation, PW dist flow maxmin, PW distance ratio. Such features may be calculated on a breath by breath basis as detected from the signals. These features are summarized below and are contained in the following Table II. Additional features are discussed in more detail below.

TABLE II

| | FEATURE LIST | |
|---|---|---|
| 1 | RR breath | Respiratory Rate |
| 2 | RR ratio | based features |
| 3 | IE ratio | |
| 4 | $Vol_I$ | Volume based |
| 5 | $Vol_E$ | features |
| 6 | breathLeak | |
| 7 | Vol ratio | |
| 8 | $PEEPi_i$ | Respiratory |
| 9 | $R_i$ | Mechanics based |
| 10 | $C_i$ | features |
| 11 | $Tau_i$ | |
| 12 | $PEEPi_e$ | |
| 13 | $R_e$ | |
| 14 | $C_e$ | |
| 15 | $Tau_e$ | |
| 16 | InterpMinima | Expiratory Flow |
| 17 | InterpMinima-⅔ | Morphology based |
| 18 | PW linear approx power | features |
| 19 | PW vol deviation | |
| 20 | PW dist flow maxmin | |
| 21 | PW distance ratio | |

Respiratory rate based features may include the following:

$RR_{breath} = 1/T_{breath}$. This respiratory rate feature may be determined on a per breath basis and values thereof can be calculated as the inverse of the period.

RR ratio=$RR_{breath}/RR_{mean}$. This feature based on the respiratory rate may be determined as the ratio of the respiratory rate of the breath to the mean respiratory rate calculated over a period of time such as 5 minutes.

IE ratio=$T_i/T_{breath}$. This feature based on the respiratory rate may be determined as the ratio of inspiratory time for the breath to the period of the breath.

Volume based features for each breath may include the following:

$Vol_I$—This determined feature may be considered an absolute volume inhaled in a breath. It may be determined as the integral of the flow during inspiration.

$Vol_E$—This determined feature may be considered an absolute volume exhaled in a breath. It may be determined as the integral of the flow during expiration.

breathLeak=$Vol_I$-$Vol_E$. This determined feature may be considered the volume leaked between inspiration and expiration. It may be determined as the difference between the absolute volume inhaled and the absolute volume exhaled.

Vol ratio=$Vol_I/Vol_E$. This determined feature may be considered a ratio of inspiratory and expiratory volumes of a breath. It may be calculated as the absolute volume inhaled divided by the absolute volume exhaled.

Respiratory Mechanics based features for each breath may also be determined. For example, mechanics parameters can be calculated for both inspiratory and expiratory phases (denoted by subscript i and e respectively) of each breath by a multiple linear regression fit of pressure, flow and volume data to a first order single compartment lung model as follows:

Pressure=Flow*$R$+Volume/$C$+PEEPtot

Where:
PEEPtot is the sum of the applied pressure during expiration and the patient's intrinsic PEEP;
R is the resistance of the respiratory system; and
C is the compliance of the respiratory system.

Tau=$R*C$. The patient's time constant (Tau), a respiratory mechanics based feature, may also be determined as the resistance times the compliance.

Expiratory flow morphology based features may also be determined. Asynchronies may be characterized by irregularities or perturbations on the pressure and flow signals. To identify these during expiration, significant deviations of the flow curve may be derived from an approximated "normal" expiratory flow shape. A segmented moving average filter with time constant, such as about 0.1 seconds, can be applied to a flow signal separately for each respiratory phase. For each period of expiration, the location of the maximum expiratory flow occurring in the first portion (e.g., 25%) of expiration was obtained. Additional expiratory flow morphology based features may include the following:

interpMinima—For the remainder of expiration beyond the first portion, local minima may be determined at discrete intervals, such as at intervals of about 150 milliseconds, for example. Interpolation from these minima for the duration of expiration can be determined. The result may be used to de-trend the moving average by subtraction, and the power (RMS) can be obtained for the resultant signal and normalised across the mode value for the patient.

interpMinima-⅔—This feature may be determined with the de-trended interpolated minima signal above. From the interpolated minima signal, the power (RMS) can be calculated for the last two thirds of expiration, and normalised across the mode value for the patient.

PW linear approx power—This feature may be considered a piecewise bilinear approximation for the remainder of expiration after the location of maximum expiratory flow. The second linear component can be used to de-trend the moving average by subtraction. The power (RMS) can then be determined for the resultant signal, and normalised across the mode value for the patient.

PW vol deviation—This feature may be considered a piecewise volume deviation. It may be calculated as the integral of the rectified and de-trended moving average. The de-trending may be determined by subtraction of the piecewise linear approximation. It can be normalised across the mode value for each patient.

PW dist flow maxmin—This feature may be considered a piecewise distance flow maximum minimum. It may be determined with indices of the minimum and maximum of the de-trended moving average (via subtraction of the piecewise linear approximation). The minimum and maximum were then used to locate the corresponding real flow values in the moving average expiratory flow signal. The distance between these two real flow values may then be calculated in the Y direction.

PW distance ratio—This feature may be considered a piecewise distance ratio. It may be determined as a ratio of the PW dist flow maxmin. It may be calculated as a fraction of the distance between the maximum flow point (calculated previously) and the peak expiratory flow.

Additional features for features sets are discussed in further embodiments below.

Feature Set Selection

Sets of the features such as the respiratory rate based features, volume based features, respiratory mechanics based features and expiratory flow morphology based features, for implementation by the detector 100 may be chosen at design time based on the indicative nature of each feature relative to a particular asynchrony event. Thus, empirical analysis of the features in association with known breath asynchrony data may be utilized to derive feature sets indicative of asynchrony and a pattern of threshold values of the features that may be suitable for use in detectors described herein. This empirical analysis may be based on data from multiple patients. For example, a classifier model, such as a Parzen Window Estimator, may be implemented to identify or select suitable feature sets. The following is a description of an example implementation of such a classifier.

Classifier Model

Parzen Window Estimation

A Parzen window estimator may be implemented by a processing apparatus to evaluate feature subsets indicative of asynchrony events by analysis of groups of features such as a superset of some or all of the above features in conjunction with the known breath asynchrony data. For example, after the above features are determined or extracted from the sensor signals, each breath may have an associated set of features, x. This feature vector will have up to X features depending on the desired application. In such a classifier, if $\omega_i$ signifies the $i_{th}$ class, a Bayes' rule methodology may be implemented to find the class for a given test feature vector that will maximize the posterior probability as follows:

$$P(\omega_i | x) = \frac{P(\omega_i) p(x | \omega_i)}{p(x)} \quad (1)$$

Posterior probability for each category may be calculated via Parzen-window estimation. An advantage of this nonparametric method is that it can be used without the assumption that the forms of the underlying densities are known. To estimate the density p (x) at x, first a sequence of regions $R_1 \ldots R_n$ is created across the feature space. Each region $R_n$ is a d-dimensional hypercube. If $h_n$ is the length of the side of the hypercube, its volume is given by:

$$V_n = h_n^d \qquad (2)$$

It follows that the number of samples falling into the hypercube $k_n$ can be defined by the following window function:

$$k_n = \sum_{i=1}^{n} \varphi\left(\frac{x - x_i}{h_n}\right) \qquad (3)$$

Where $\phi(u)$ is a unit hypercube having the value one inside and the value zero outside the unit hypercube centred at origin. Combing (2) and (3), the Parzen-window density estimate using n training samples and the window function can be defined by:

$$p_n(x) = \frac{1}{n} \sum_{i=1}^{n} \frac{1}{V_n} \varphi\left(\frac{x - x_i}{h_n}\right)$$

A Gaussian window function may be used with radius equal to the median of the Euclidean distances between feature vectors.

Due to the possibility of the estimator being applied to breath data that is labelled with multiple classes, the classifier can be operated as a dichotomizer such that each class can be treated separately and sequentially.

Feature Subset Selection

The processing apparatus can be implemented with a form of a sequential selection algorithm, such as the Sequential Forward Floating Search (SFSS) algorithm, to serve as a subset selector that can identify the feature subset that maximizes a classification performance criterion. For example, an accuracy criterion may be calculated as the percentage of breaths correctly classified with each subset based on the known classification. Initially, such an algorithm can make several (e.g., 3) passes with the ordinary sequential forward selection (SFS), such that three features are selected. Each of these evaluation passes adds the particular feature that contributes the greatest improvement to performance over and above the performance threshold of the already selected features. To avoid "nesting" of features that are not part of the optimal feature set, features can be removed one at a time and the sequence of the remaining features can be re-shuffled. The classifier performance may then be checked for any improvement. New combinations of features are only chosen subsequent to an improvement in performance. Following such a feature trimming phase, the SFS algorithm can then run to add a new feature. This cycle of feature addition and trimming iterates until performance of a particular feature subset has been maximized.

Example Feature Sets

For example, one embodiment of a detector 100 designed by such a process can be implemented with a subset of features for detecting expiratory ineffective effort asynchrony. Such a subset may include PW linear approx power, PW dist flow maxmin, PW vol deviation, $Tau_i$ and PW distance ratio. Values for these features on a breath-by-breath basis may be calculated from the respiratory apparatus sensor data and compared to a corresponding set of thresholds to detect the existence of the expiratory ineffective effort asynchrony event in one or more breaths. Additional feature set examples are discussed in more detail herein.

Experimental Testing

Based on the aforementioned methodologies, 5627 breaths from 23 patients in a pulmonary ward were examined. The patients were undergoing both conventional and non-invasive ventilation (NIV). Patients were undergoing NIV after recovering from acute respiratory failure or conventional ventilation in the advanced stage of weaning. For each subject between 10-20 minutes of respiratory data was obtained. The following traces were obtained. Flow at the airway opening was measured with a heated pneumotachograph and a differential pressure transducer placed between the mask and the Y-piece of the ventilator or at the Y-piece. Airway pressure was measured from a side port between the pneumotachograph and the face mask or the endrotracheal tube. Esophageal and gastric pressures were measured with a balloon-catheter system. To this end, an esophageal balloon was positioned at the lower third of the esophagus, filled with 0.5 ml of air and a gastric balloon filled with 1 ml of air. The proper position of the balloon was verified using the occlusion test. Transdiaphragmatic pressure (Pdi) was calculated as the difference between gastric (Pga) and esophageal (Pes) pressures.

Breath Segmentation Algorithm

Figure 10:
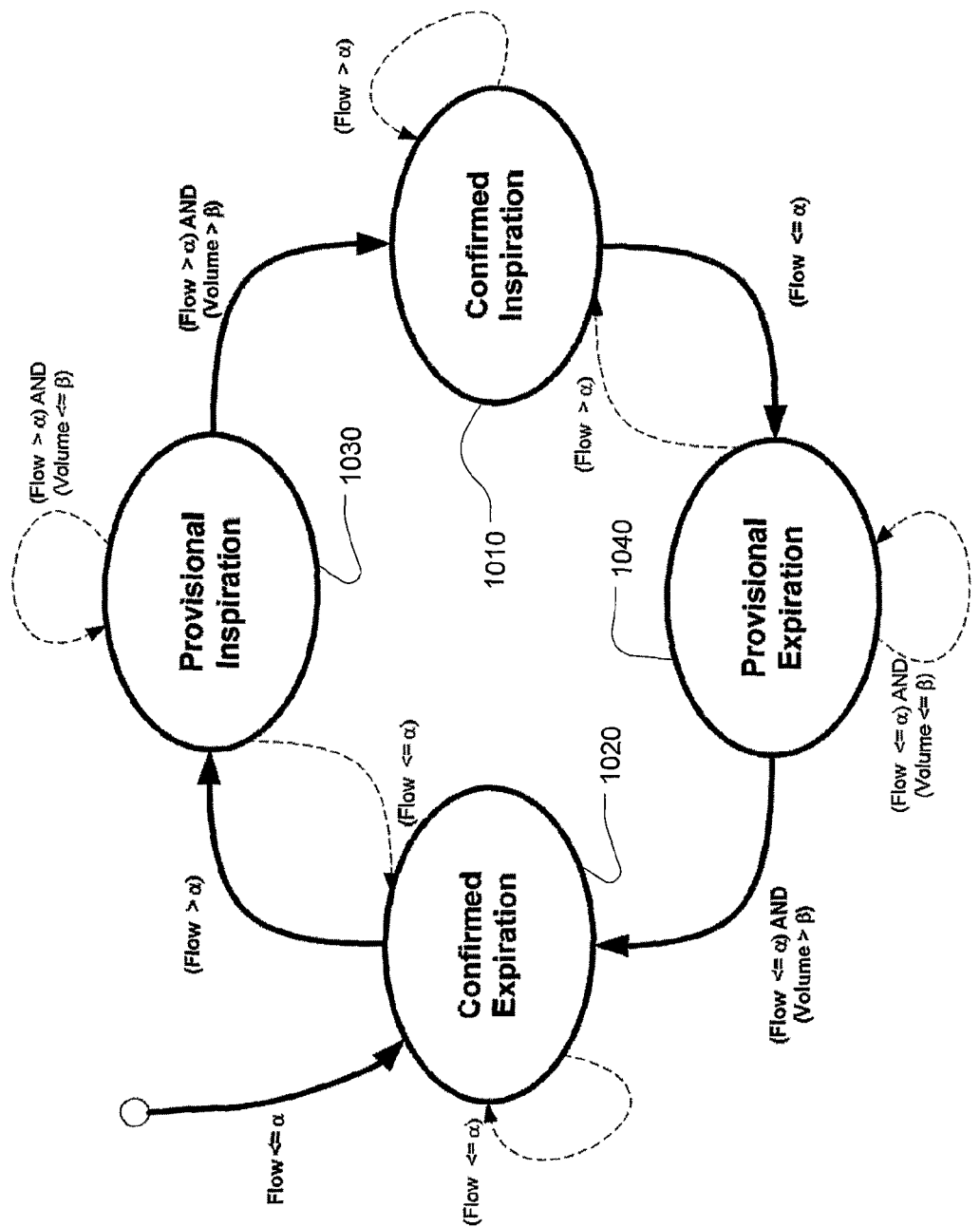
FIG. 10 is an diagram for a state machine to detect respiration related states in some embodiments of the technology.

A segmentation algorithm was applied to the data with the processing apparatus to automatically demark each breath instance. As illustrated in FIG. 10, the programmed state-machine included four states and analyzed the flow and volume signals (shown as "Flow" and "Volume" conditions of FIG. 10) to identify the points in time at the beginning and end of each inspiration. This identification corresponded to the state machine entering the "Confirmed Inspiration" state 1010 and the "Confirmed Expiration" state 1020 shown in FIG. 10 based on the flow and volume conditions. The chosen flow and volume thresholds expressed in the conditions of the state diagram logic are $\alpha=0.05$ L/s and $\beta=150$ mL. Other methods of breath demarcation might also be implemented.

As illustrated in FIG. 10, and starting in the Confirmed Expiration state 1020, the programmed processor waits for the flow to be greater than a positive value near zero ($\alpha$) before it advances into the Provisional Inspiration state 1030. Then, only when it detects sufficiently accumulated volume ($\beta$) to indicate that the signal is established in inspiration beyond noise fluctuations close to zero, does the processor advance to the Confirmed Inspiration state 1010. A similar processing logic applies to the transition from the Confirmed Inspiration state 1010 through Provisional Expiration 1040 and back to the Confirmed Expiration state. By monitoring these locations in time relative to the data of the flow signal, times are identified at the beginning and end of each inspiration, corresponding to when the state machine enters the Confirmed Inspiration and the Confirmed Expiration states.

Visual Asynchrony Scoring

Visual scoring of asynchronies and correction of breath demarcation was carried out by a single physician specializing in mechanical ventilation using a custom designed graphical user interface (Matlab). Alternately, an automated computer system may be utilized to calculate the scoring of the asynchronies.

Figure 13:
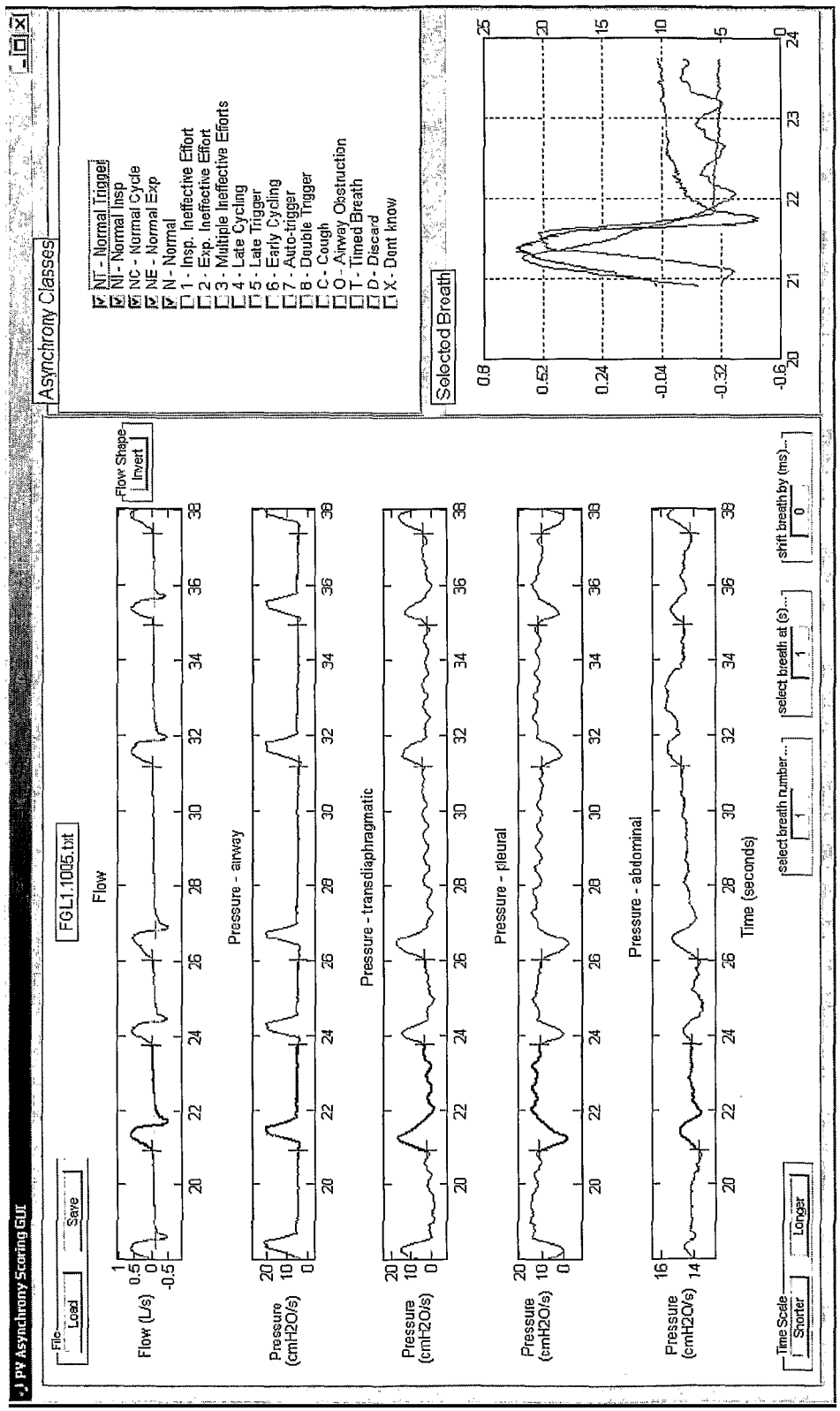
FIG. 13 is a screenshot of an example user interface suitable for manual classification of asynchrony events.

An example graphic user interface (GUI) for manual event scoring is illustrated in FIG. 13. The interface permits manual scoring by easy visual assessment of each and every breath individually and within the context of the breath series. The interface allows categorization according to its display and navigation through the signals. Data files with the data of the signals may be managed with buttons in the top right corner of the interface. On loading a data file, the program of the interface parses data headers as variable names and stores the column data accordingly. Files with saved data may include a reserved set of workspace variables reserved as follows:

CompFlow:
Patient flow data compensated for offsets and leak.
Pao:
Pressure at the airway
Pdi:
Transdiaphragmatic pressure
Ppl:
Pleural pressure
Pab:
Abdominal pressure
Inspirations:
Array of indices demarking the beginning of inspiration for each breath
Expirations:
Array of indices demarking the beginning of expiration (accordingly, the end of inspiration) for each breath
AsynchronyClass:
Array of labels designated to each breath indicating the types of asynchrony present if any
Fs:
Sampling rate of the data, default at 100 Hz
Filename:
Unique file identifier In the example interface, five plots are used to display the time series data which from top-to-bottom, including the patient flow, pressure at the airway, transdiaphragmatic pressure, pleural pressure, and abdominal pressure. A control button may be included to allow inversion of the flow if necessary.

The time scale of the data may be adjusted by the button groups in the bottom left hand corner of the panel. For example, shortening of the scale may halves the range of seconds displayed and conversely lengthening the scale may double the range. Navigation through the data is achieved by flipping forward or backwards screen by screen according to the time scale set via up and down arrow keys of a keyboard of the computer programmed with the interface. Markers can be shown on the data traces indicating the beginning of both inspiration and expiration for every breath as demarked by an automated breath detection algorithm as discussed in more detail herein. One breath can be selected and the corresponding portions of each trace are then highlighted at any one time. A breath can be selected either by using the left and right arrow keys to move sequentially forwards and backwards, or entering numeric information (breath number or time at which the breath occurs) into the first two user input boxes in the bottom right hand corner of the panel. The denoted start of inspiration for a breath can be adjusted by entering an offset in milliseconds in the last user input box.

The bottom right panel of the interface shows a more detailed graph of a single breath, where the patient flow, pressure at the airway and transdiaphragmatic pressure are overlaid on common graphing axes. The pressure scale is given on the left axis and the flow on the right. This allows the scorer to view timing detail of the signals with greater resolution.

Finally, the upper right panel functions to receive and store user input regarding the categorization of the breaths with checkboxes. More than one category may be checked at a time. The categories available to choose from and their definition criteria may include:

Normal Trigger:
The triggering of the ventilator is reasonably coordinated with respect to the beginning of the patient's effort.
Normal Inspiration:
The interaction between the ventilator and patient during inspiration is harmonious.
Normal Cycle:
The cycling of the ventilator is reasonably coordinated with respect to the termination of the patient's effort.
Normal Expiration:
The interaction between the ventilator and patient during expiration is harmonious.
Inspiratory Ineffective Effort:
A positive Pdi tidal swing beginning after the ventilator has triggered and is delivering inspiratory support, resulting in an increasing swing in the flow trace.
Expiratory Ineffective Effort:
A positive Pdi tidal swing occurred during expiration, but was not followed by inspiratory support from the ventilator.
Multiple Ineffective Efforts:
Two or more positive Pdi tidal swings occurring during expiration, where none are followed by inspiratory support from the ventilator.
Late Cycling:
A positive tidal swing occurs in Pdi during expiration that is not followed by inspiratory pressure support from the ventilator until more than 150 ms has elapsed. The increase in Pdi indicates that the start of patient effort was more than 150 ms after the device delivered pressure support.
Late Trigger:
A prolongation of the ventilator's inspiratory time beyond the end of the patient's inspiratory effort. For example, where $Ti_{excess}$ is the prolongation of the ventilator inspiratory time beyond the end of patient effort; and $Ti_{pat}$ is the duration of patient inspiratory effort, a late trigger may be considered to exist when the time $Ti_{excess}$ is greater than half of the time $Ti_{pat}$, $Ti_{excess} > Ti_{pat}/2$)
Early Cycling:
A termination of inspiratory support by the ventilator prior to the end of the patient's Pdi tidal swing, indicating that the patient's effort is prolonged beyond the device's mechanical breath.
Auto-trigger:
The delivery of inspiratory support by the respiratory treatment apparatus or ventilator without a concomitant swing in Pdi that would otherwise indicate patient effort. This can be taken to indicate that the device delivered a breath that was not triggered by the patient.
Double Trigger:
Two mechanical breaths over a single Pdi tidal swing are delivered. The first cycle is patient-triggered and separated from the second by a very short expiratory time that may be defined as being less than about one-half of the mean inspiratory time of previous normal breaths.

Cough:
The patient is coughing indicated by large negative spike in expiration with abdominal effort.

Airway Obstruction:
The upper airways are largely obstructed, as indicated either by flattened or no flow concomitant with patient effort, or briefly during a swallowing manoeuvre occurring predominantly in expiration.

Timed Breath:
A mandatory breath triggered by the ventilator.

Discard:
The data is corrupted and not suitable for use.

Don't Know:
The event/activity is ambiguous and needs further review.

The physician designated to carry out the visual scoring was blinded to the clinical data of the patients and was not involved in their care.

The beginning of inspiration was globally adjusted for each patient by 200 ms (±50 ms) to align with the deflection of Pdi corresponding to the initiation of patient effort. Subsequently, each breath was labeled as either normal or asynchronous by the categories and definitions of the asynchronous events previously identified including, expiratory ineffective effort events, post-triggering effort events, double triggering events, autotriggering events, late triggering events, early cycling events, late cycling events and inspiratory ineffective effort events.

The total of 5627 breaths were analyzed and labeled as summarized in Table II below.

TABLE II

SUMMARY OF VISUAL CLASSIFICATIONS

| Category | Count | % of Total |
| --- | --- | --- |
| Normal | 2960 | 52.63 |
| Expiratory Ineffective Effort | 567 | 10.08 |
| Inspiratory Ineffective Effort | 93 | 1.65 |
| Double Trigger | 48 | 0.85 |
| Auto-trigger | 77 | 1.37 |
| Late Trigger | 811 | 14.42 |
| Early Cycling | 527 | 9.37 |
| Late Cycling | 646 | 11.49 |
| Other events | 300 | 5.33 |
| Unknown | 276 | 4.91 |
| Physical breaths | 5624 | 100 |
| Total classifications | 6305 | 112.11 |

Feature Selection

As a goal of this experiment was to automate the detection of asynchronies via non-invasive sensors, a superset of detection features were derived using only the flow and pressure signals rather than with the transdiaphragmatic pressure signal. Thus, a programmed processing apparatus derived features for each breath based on data from the flow and pressure signals. The derived features were those summarized previously in Table I above.

Parzen Window Estimator and Feature Subset Selector

The feature data was then applied to a processing apparatus with a programmed parzen window estimator and feature subset selector as previously described. In testing, the data was analyzed to develop a feature set for an ineffective efforts asynchrony event classifier. Additional, feature sets for the remaining asynchrony events may be similarly developed.

Cross-Fold Validator

Cross-fold validation was applied to assess the results of the developed asynchrony classifier. To this end the superset of features from all but one patient formed the training data for the development of the detector/classifier. The classifier with the subset of features was then tested on the corresponding feature data of the excluded patient. This process was iterated 23 times for all patients, whereby one patient was excluded from the training data and reserved to test the automatic asynchrony detection system in each iteration. In other words, the classifier that was automatically developed with the data from the larger group of patients was then used to automatically detect the asynchrony events from the data of the excluded patient. Accuracies, sensitivities, specificities, positive and negative predictive values and Cohen's kappa coefficient were then averaged across all 23 passes for overall estimate of performance of the detector/classifier.

Testing Results

Table III below contains the positive predictivity, negative predictivity, sensitivity and specificity results for the detections made by the automated asynchrony detector using a developed feature set for detecting ineffective effort asynchrony events. The performance of the detector was compared to the manually annotated data for 5627 breaths. Also shown is the number of records, N, for which each parameter that was calculable. The feature subset for the example detector selected in order were: 1. PW linear approx power; 2. PW dist flow maxmin; 3. PW vol deviation; 4. Tau$_i$; and 5. PW distance ratio.

TABLE III

PERFORMANCE RESULTS FOR INEFFECTIVE EFFORTS CLASSIFICATION

| Measure | Mean |
| --- | --- |
| Positive Predictivity | 84.03% |
| Negative Predictivity | 95.32% |
| Sensitivity | 58.74% |
| Specificity | 98.69% |
| Overall Accuracy | 94.49% |

Experimental Testing Assessments

A non-invasive method for detecting major forms of asynchrony in patient-ventilator interaction has been designed and compared to a human expert-based classification system using a database of 23 subjects.

In the case of classifying expiratory ineffective efforts, overall accuracy and specificity of the detector/classifier is high, whereas the sensitivity is moderate. Possible causes for the lower sensitivity relate to the fact that timed pressure support breaths were common amongst the data. In such modes containing these breaths, it is intentional for the ventilator to ignore normal efforts exerted by the patient, preferring to dictate the timing in a metronomic fashion. As a result, normal size efforts may influence the flow signal producing normal positive swings that are not accompanied by pressure support. These efforts, while still classed as ineffective, are not the pathological variety, influenced largely by intrinsic PEEP and hyperinflation, which preoccupy the main concern of clinicians for patients on pressure support ventilation. Pathologic ineffective efforts occur with smaller and negative value flow swings relative to their timed mode induced counterparts. As such, the combined feature vectors intersect a greater proportion of other breath classes. Relabeling of this class as two subsets may improve the sensitivity of the classifier.

Another factor influencing the sensitivity of the classifier is the similar morphology between expiratory efforts and early cycling: both are categorized by a single perturbation on the flow signal during expiration (and correspondingly on the pressure), however are distinguished merely by distance in time they occur from the start of expiration. This distance is subject dependent, and may be ambiguous even by expert visual inspection.

Factors limiting classifier specificity include artifacts such as coughs, swallowing, and abdominal effort, as well as incorrect breath labeling brought about by human error and ambiguity where the Pdi signal is noisy, exhibits large drifts, or where esophageal spasms occur.

It is interesting to note that as well as morphological features, the inspiratory time constant $Tau_i$ was selected as a distinguishing feature by the SFSS algorithm. It is interesting to relate this physiological parameter to the mechanism of ineffective efforts, which occur predominantly in obstructive patients with hyperinflation. We could expect then, that patients with high inspiratory time constant exhibit a greater number of ineffective efforts.

In sum, using a pattern classification approach to automating the detection of asynchronies is feasible and may be of clinical utility in assessing the quality of patient ventilator interaction.

Example Expiratory Ineffective Efforts Related Feature Sets

In some embodiments of the detector, feature sets may be specially devised for one or more particular asynchrony events. For example, often asynchronies are characterized by irregularities or perturbations on the pressure and flow signals. Specifically with respect to expiratory ineffective effort events (eIEs), these irregularities occur during expiration. As the signal-to-noise ratio of these irregularities is generally higher on the flow signal than on the pressure signal, flow may be used as the main signal for deriving the feature set. To this end, a segmented moving average filter with time constant of about 0.1 seconds may be applied to the flow signal separately for each respiratory phase. In order to identify irregularities during expiration, significant deviations of the flow curve from a more 'normal' predicted trajectory of the breath's expiratory shape may be derived. We call this predicted trajectory through expiration, $\Theta$. The predicted trajectory may be used to detrend the filtered flow signal, $\dot{V}_f$, by subtraction as follows:

$$\Phi = \dot{V}_f - \Theta$$

such that the resultant signal, $\Phi$, emphasized any irregular deviations that may represent asynchronies. Features were derived from further operations on $\Phi$.

Figure 14A:
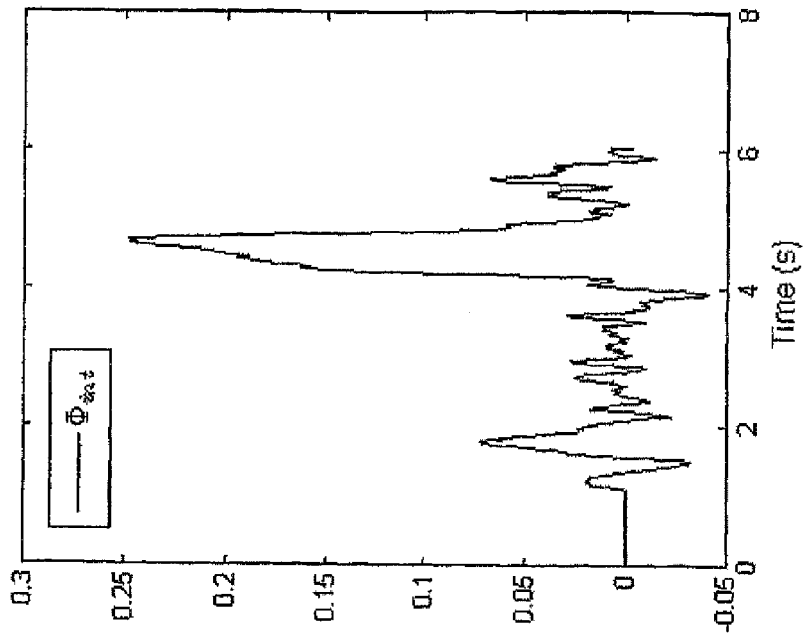
FIGS. 14(a) and 14(b) are graphs illustrating steps of an automated process or analysis of expiratory flow and an output signal with an indicator of an expiratory ineffective effort asynchrony event from which features may be determined.
Figure 14B:
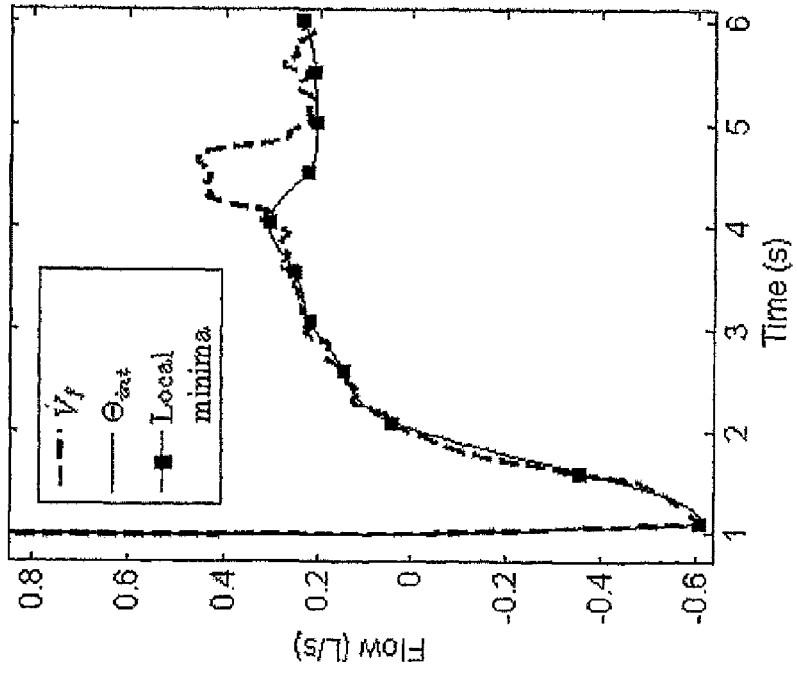

The predicted trajectory through expiration signal $\Theta$ may be derived by one of two example methods as follows. Initially for both methods, the location of the maximum expiratory flow occurring in the first 25% of expiration was obtained. Up until this location, $\Theta$ was equivalent to the filtered flow. Thereafter, the remainder of $\Theta$ may be calculated by one of the following methods:

(1) Interpolated minima method:
Local minima may be obtained at intervals of 500 ms from the filtered flow signal. $\Theta_{int}$ can be derived by interpolation from these minima between the maximum expiratory flow and the end of expiration. FIGS. 14(*a*) and 14(*b*) illustrate the method applied to an expiratory sample containing an expiratory ineffective effort. In FIG. 14(*a*), the filtered expiratory flow data, $\dot{V}_f$ contains an expiratory ineffective effort. The derivation of the predicted normal trajectory, $\Theta_{int}$, entails finding local minima at 500 ms intervals of the data occurring after the peak expiratory flow, and interpolating between the minima to derive a smoother version of the original. The signal $\Phi_{int}$, which is obtained by subtracting $\Theta_{int}$ from $\dot{V}_f$, highlights or indicates the ineffective effort.

Figure 15B:
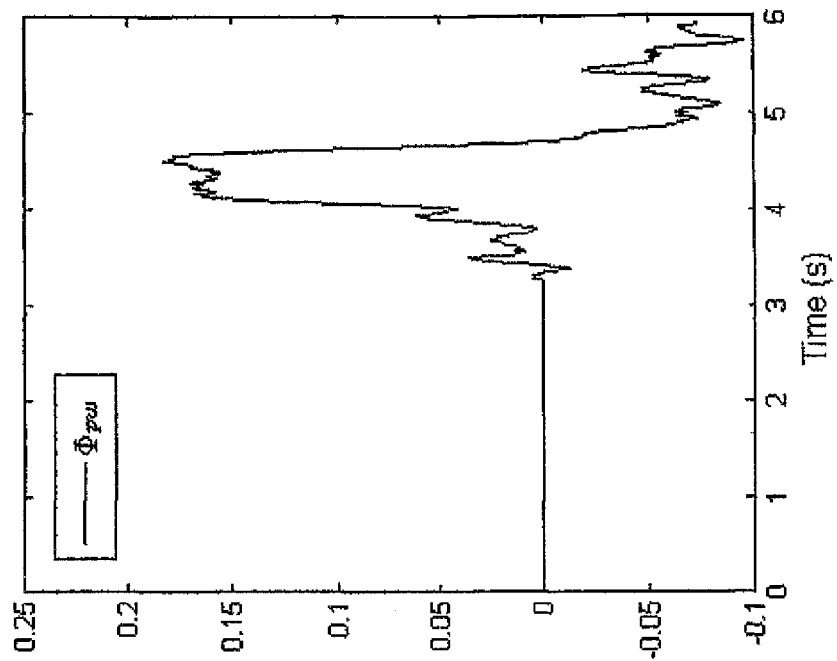
FIGS. 15(a) and 15(b) are graphs illustrating further steps of an automated process or analysis of expiratory flow and an output signal with an indicator of an expiratory ineffective effort asynchrony event from which features may be determined.
Figure 15A:
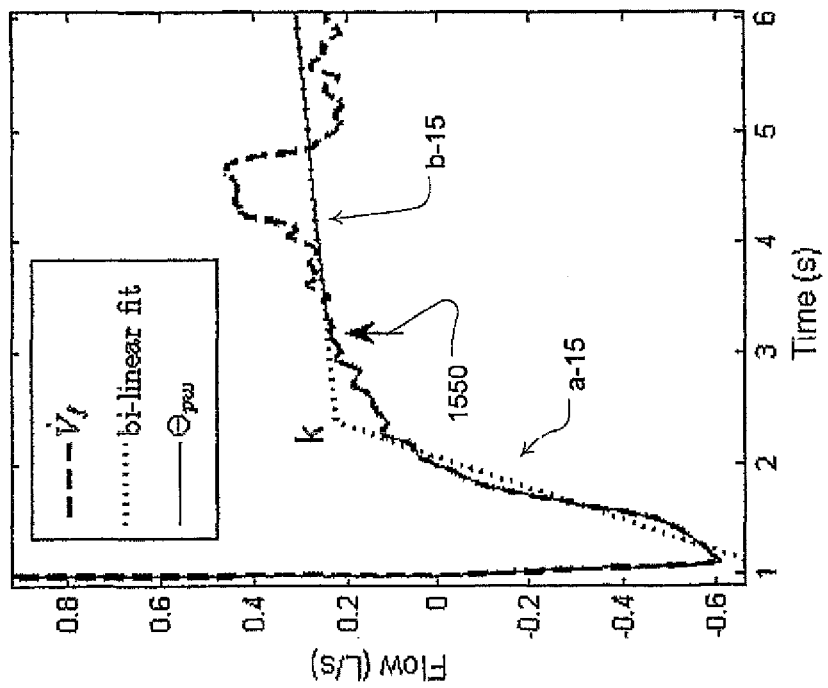

(2) Piecewise bilinear fit method:
A piecewise bilinear approximation may be performed for the remainder of expiratory flow data after the location of maximum expiratory flow. This procedure may involve least squares fitting of the data to two linear sections, shown as a-15 and b-15, which can be continuously linked by an elbow or breakpoint at location k. In order to determine where the breakpoint needed to be so as to offer the best and most appropriate fit, values of k may be tested sequentially from the first sample to that equal to a third of the length of the data. The test condition can be the root-mean-square of the differences between the data and the fitted values, and the k that returned the minimum condition value can be chosen. The location of k may be restricted to the first third of expiration because a typical expiratory profile changes its curvature most distinctly within this nominal period. Furthermore, ineffective efforts tended to occur most commonly during the latter two thirds of expiration. For the purposes of emphasizing the ineffective effort in the calculation of $\Phi_{pw}$, a linear fit that had higher variance around the region pertaining to the ineffective effort feature was desirable. If no restriction was put on the placement of k, it may be the case that for expirations containing ineffective efforts, the best k would locate within the ineffective effort morphology itself, and thus render the procedure inadequate for augmenting it. The signal $\Theta_{pw}$ may be derived by concatenating the filtered flow up to its first intersection with the second linear component, b-15, and the remaining portion of b-15 beyond this intersection. FIGS. 15(*a*) and 15(*b*) show the method applied to the same sample shown in FIGS. 14(*a*) and 14(*b*). Thus, in FIG. 15(*a*), the filtered expiratory flow data, $\dot{V}_f$ contains an expiratory ineffective effort. The derivation of the predicted normal trajectory, $\Theta_{pw}$, may entail fitting a piecewise bilinear function (sections a-15 and b-15 joined at breakpoint k) to the data after the location of the maximum expiratory peak, and concatenating the second linear component to the filtered flow at their intersection (indicated by the upwards arrow 1550). The signal $\Phi_{pw}$, which may be obtained by subtracting $\Theta_{pw}$ from $\dot{V}_f$, highlights or indicates the ineffective effort.

Figure 16:
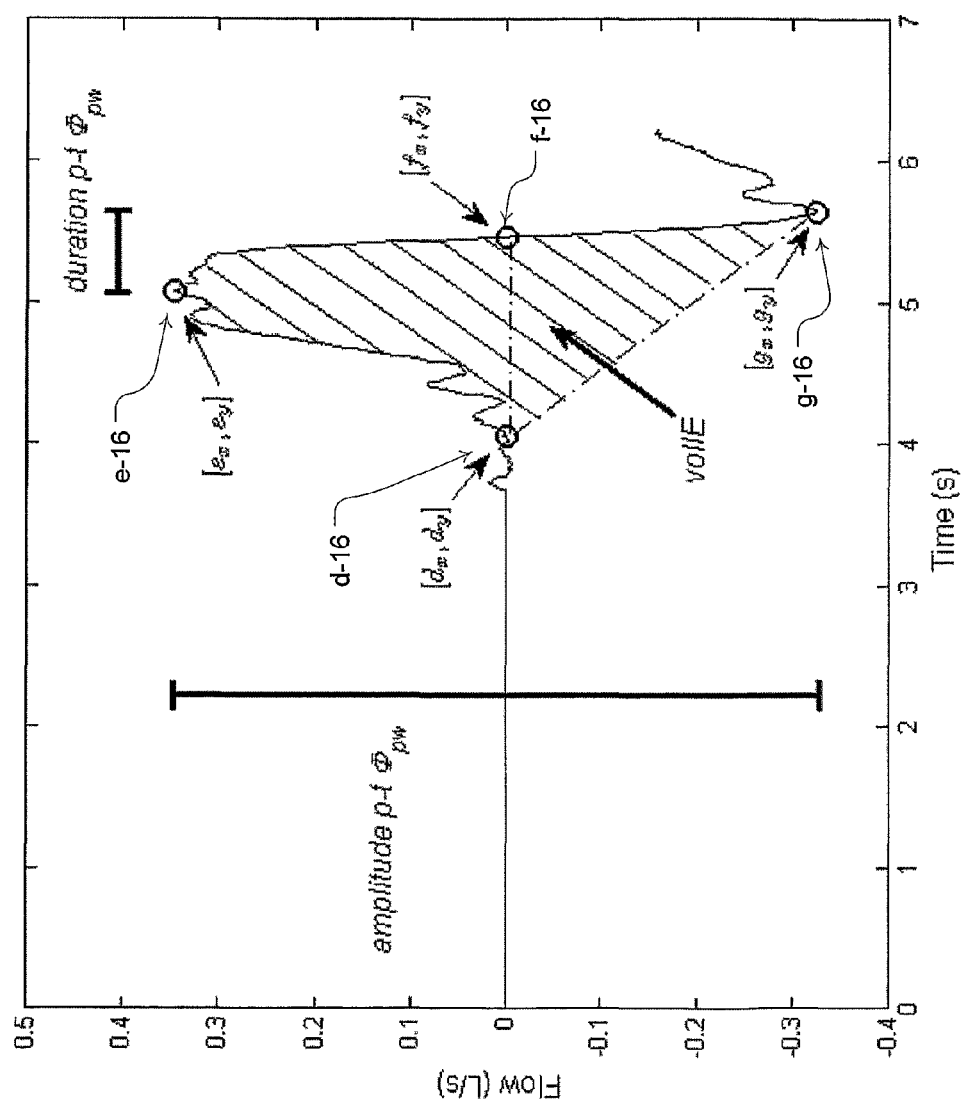
FIG. 16 is a graph illustrating additional aspects of an automated analysis in the determination of some features suitable for detecting expiratory ineffective effort asynchrony events.

Fiducial points may be located on $\Theta_{pw}$ with the data of the signal to derive the feature set using these traces. Examples are illustrated in FIG. 16, which shows the detrended flow, $\Theta_{int}$, marked with fiducial points shown on FIG. 16 as d-16, e-16, f-16 and g-16. The points may include the following:

d-16: $[d_x, d_y]$, the zero-crossing with positive slope occurring immediately prior to the maximum value;

e-16: [$e_x, e_y$], the maximum value;

f-16: [$f_x, f_y$], the zero-crossing with negative slope occurring immediately after the maximum value, that also occurs prior to the minimum; and g-16: [$g_x, g_y$], the minimum value.

Figure 17:
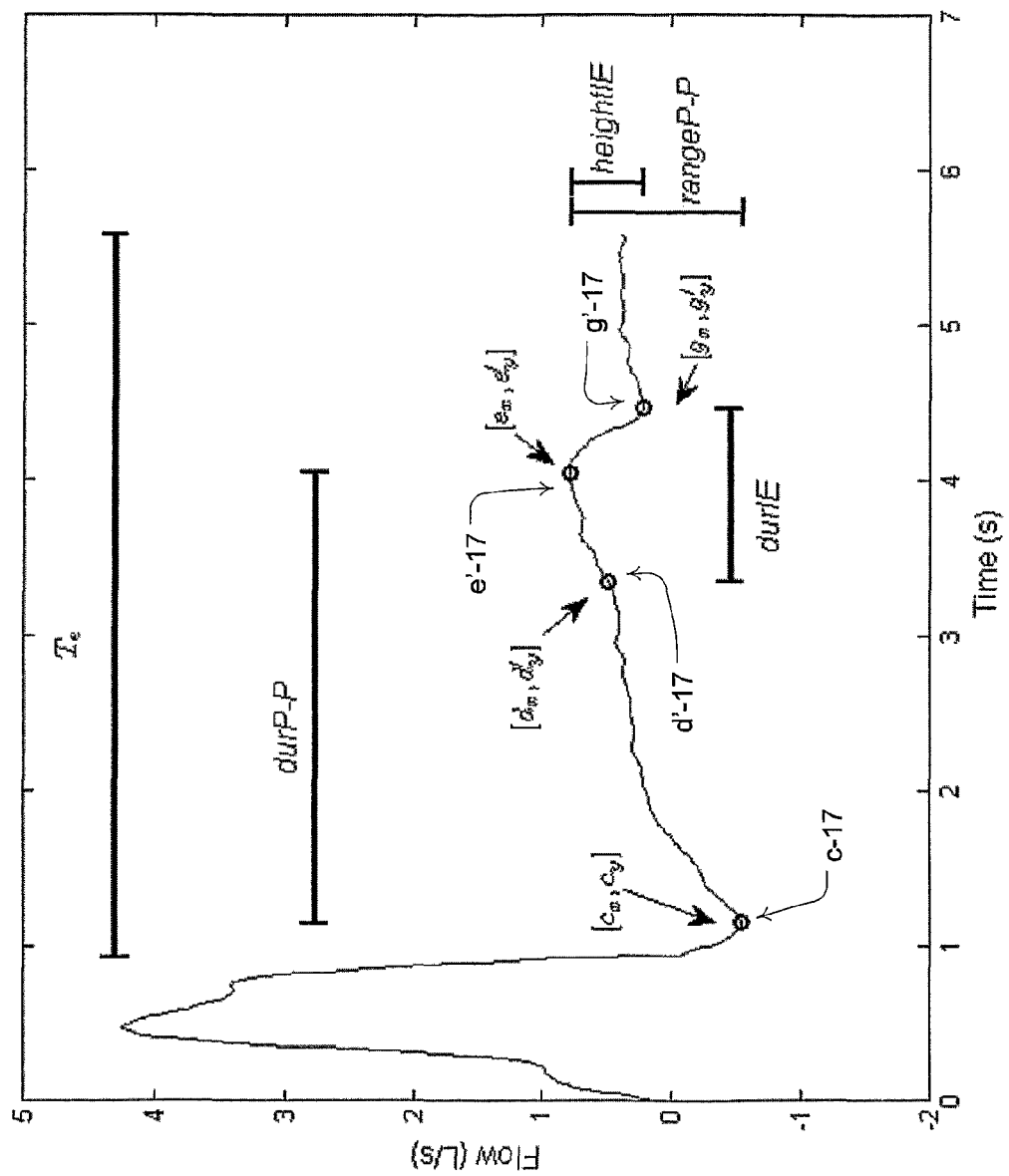
FIG. 17 is a graph illustrating further aspects of an automated analysis in the determination of some features suitable for detecting expiratory ineffective effort asynchrony events as well as illustrating some of the features.

These fiducial points may be mapped to the data of the filtered flow, $\dot{V}_f$, contributing to its complete fiducial point set. This is illustrated in FIG. 17, which shows the filtered flow, $\dot{V}_f$, marked with fiducial points labeled as c-17, d'-17, e'-17, f'-17 and g'-17. These points may be considered as follows:

c-17: [$c_x, c_y$], the peak expiratory flow on the filtered flow, $\dot{V}_f$ d'-17: [$d_x, d'_y$], the onset of the ineffective effort e'-17: [$e_x, e'_y$], the peak value of the ineffective effort g'-17: [$g_x, g'_y$], the completion of the ineffective effort One or more of the following features may then be derived from $\Phi_{pw}$ and $\Phi_{int}$, and where possible are illustrated in FIGS. 16 and 17.

power $\Phi_{int}$:
This feature may be considered the power (RMS) of $\Phi_{int}$, given by $$\Phi_{rms} = \sqrt{\frac{\sum \Phi_i^2}{n}}$$

where i is the sample number, and n is the number of samples in the signal;

power $\frac{2}{3}\Phi_{int}$:
This feature may be considered the power (RMS) of the last two thirds of $\Phi_{int}$;

power $\Phi_{pw}$:
This feature may be considered the power (RMS) of $\Phi_{pw}$;

integral $\Phi_{pw}$:
This feature may be considered the integral of $\Phi_{pw}$ after rectification equivalent;

gradient-a:
This feature may be considered the gradient of the first linearly fitted section, a-15;

gradient-b:
This feature may be considered the gradient of the second linearly fitted section, b-15;

amplitude p-t $\Phi_{pw}$:
This feature may be considered the vertical distance between the maximum and minimum values in $\Phi_{pw}$, $e_y$-$g_y$; duration p-t $\Phi_{pw}$:
This feature may be considered the horizontal distance between the maximum and minimum values in $\Phi_{pw}$, $g_x$-$e_x$;

volIE:
This feature may be considered the volume of air moved during the ineffective effort. This may be calculated by adding the positive area under the curve d-16→e-16→f-16 and the absolute value of the area enclosed by d-16→f-16→g-16→d-16 or, the integral of the arc d'-17→e'-17→g'-17 with respect to the line d'-17→g'-17;

zxUpCount:
This feature may be considered the number of zero crossings in $\Phi_{pw}$ with positive slope;

maxFlowIE:
This feature may be considered the value of the maximum flow reached in the ineffective effort, $e'_y$.

heightIE:
This feature may be considered the vertical distance between the values in $\dot{V}_f$ corresponding to the indices $e'_y$ and $g'_y$;

durIE:
This feature may be considered the duration of the ineffective effort, $g_x$-$d_x$;

rangeP-P:
This feature may be considered the vertical distance between the maximum expiratory peak in expiration and the local maxima in the ineffective effort, $e'_y$-$c_y$;

durP-P:
This feature may be considered the horizontal distance between the maximum expiratory peak in expiration and the local maxima in the ineffective effort, $e_x$-$c_x$;

ampRatio:
This feature may be considered the ratio of heightIE to rangeP-P;

volRatio:
This feature may be considered the ratio of the volume of air moved during the ineffective effort, volIE, and the total expired volume, volE.

durRatio:
This feature may be considered the ratio of the ineffective effort duration, durIE, to the length of expiration, $T_e$;

locationIE:
This feature may be considered the location of the ineffective effort in expiration calculated as the ratio of $e_x$ to the length of expiration, $T_e$;

A feature set or subset of the above expiratory flow morphological based features may be used in both original and normalized forms. Normalization may be performed such that values may be divided by the mode value for each patient. In testing as discussed above, it may be assumed that as the majority of breaths for a patient are 'normal' (without asynchronies), the mode or most frequently occurring values of a given feature would represent those breaths with normal patterns. The normalization process is intended to reduce inter-subject variability. Once the feature set is derived for each patient, the range of values for each feature and corresponding histograms may be calculated. Feature values may be assigned a bin number based on a bin width equal to about 5% of the range. The feature mode value can then be calculated as the highest density bin number multiplied by the bin width, added to the minimum feature value. Thus, as with other features previously discussed, in some embodiments the feature mode value relative to each feature determined from multiple patients may then be implemented as a threshold for detection of asynchrony events when compared to a particular feature calculated by a detector. However, in some embodiments, such a feature mode value relative to each feature may be specifically determined for past data of one particular patient and utilized for future detection with that particular patient.

As will be apparent from the aforementioned discussions, the detection of respiratory events, such as the different types of asynchrony events described herein, may be based on one or more features derived from signal morphologies (e.g., flow and/or pressure signal morphologies). This determination of features for events may also involve the identification of fiducial points, distances related thereto, ratios or other relationships between them. The automated identification of the fiducial points may include various operations such as finding zero crossings, local maxima and minima of the originally acquired physiological signals or any intermediate signals. Intermediate signals may be derived from original signals (such as flow or pressure), by mathematically fitting the data by MLR, or other functions such as linear, quadratic, exponential, sinusoidal, trapezoidal, or triangular, or piecewise combination of the above. The configuration of piecewise functions may include implementation of an optimization routine that seeks to locate breakpoints with a minimum error of fit. Intermediate signals, furthermore, can be derived from operations on one or more other intermediate signals (e.g. subtraction, superposition, desampling, interpolation). In such processes, the fiducial points may be one or more of the following examples: (a) the inflection point on a pressure signal prior to the supra plateau pressure; (b) the inflection point indicating maximum change in slope on a flow signal after the inspiratory peak and before the of end inspiration; (c) an inflection point indication maximum change in negative slope on the pressure at end expiration and immediately prior to triggering; (d) the minimum pressure immediately prior to triggering; (e) the inflection point indicating maximum change in positive slope on the flow signal during inspiration until the inspiratory peak; and/or (f) breakpoints between piecewise functions fitted to data.

Example Double Triggering Related Feature Sets

Characteristic to double triggering is rapid retriggering to form a 'rabbit-ears' pattern on the pressure signal. This pattern may be taken into account for purposes of devising feature sets for use by a suitable detector. In this regard, the flow signal will commonly follow the 'rabbit-ears' pattern, with a jagged profile revealing a retardation of inspiration that may either remain positive throughout the breath, or dip briefly into expiration ('false expiration') and return to inspiration concomitant with the re-trigger (see FIG. 5). It is desirable that the breath framer recognize this pattern as pertaining to a single inspiration. However, if the flow becomes negative between pressurizations and the corresponding volume is greater than about 150 mL, it is possible that two breaths are segmented.

Figure 18:
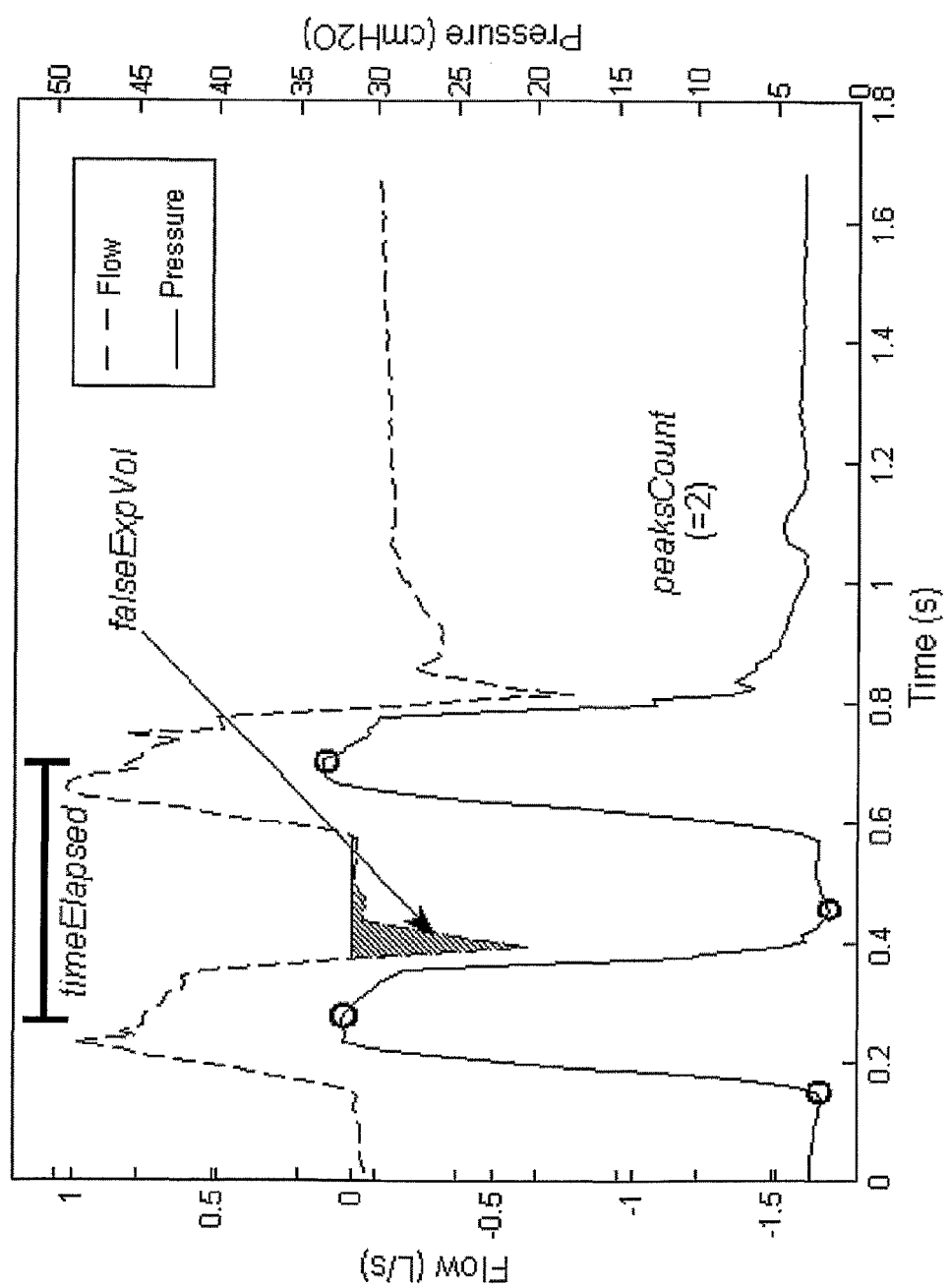
FIG. 18 is a graph illustrating aspects of an automated analysis in the determination of some features suitable for detecting double triggering asynchrony events as well as illustrating some of the features.

The following morphological features may be derived, based on these patterns, some of which are illustrated in FIG. 18. The figure shows flow and pressure signals of a breath with double triggering. Significant peaks and troughs are circumscribed, and the features of 'peaksCount', 'falseExp' and 'timeElapsed' described below are illustrated.

peaksCount:
This feature may be considered the number of significant maxima separated by significant minima more than about 5 cmH2O away. The simulated real-time peak-trough finding algorithm is described as follows. If f(x) represents a signal where x is a datum, the following action is taken on each x:
1. If f(x)>Tmax, let Tmax=f(x). Tmax is the current transitory maximum which acts as a holding variable.
2. If f(x)<Tmin, let Tmin=f(x). Tmin is the current transitory minimum which acts as a holding variable.
(Steps (1) and (2) may oscillate around noise. Until a significant difference between Tmin and Tmax is evident, Lmax and Lmin, the local maximum and minimum values, are not confirmed.)
3. If Tmax−Tmin>5 cmH2O, set Lmax=Tmax and Lmin=Tmin.
4. If we have started to descending from a peak, and f(x) is less than 75% of the range between Lmax and Lmin, set the descending flag, nullify the ascending flag, reset the transitory variables, and confirm storage of the new set of Lmax and Lmin values.
5. If we have started to ascend from a trough, and f(x) is greater than the midpoint between the most recent Lmax and Lmin, set the ascending flag, nullify the descending flag, set Lmin=Tmin, and Tmax=f(x).
6. Iterate next datum . . . .

timeElapsed:
This feature may be considered the time elapsed between significant maxima.

falseExpVol:
This feature may be considered the total expiratory volume occurring during inspiration. It is considered that this will most often be greater than 0 mL but less than 150 mL for double triggers, comprising a false expiration.

expRatio:
This feature may be considered the ratio of the current expiration time to the mean expiratory time calculated over the preceding two minutes. It may occur infrequently that the false expiration volume may be greater than 150 mL and the breath framer will erroneously split the breath. In this instance, the scorer was instructed to categorise the first breath as a double trigger. In this case, it is expected that the false expiration volume will be small relative to the average expired volume, contributing to the hyperplane separating the normal and double trigger breaths.

Thus, one or more of these double triggering related features may be calculated or determined by an automated detection processor for a particular patient and be assessed against suitable threshold(s) to determine whether a double triggering event has occurred.

Respiratory Mechanics Based Feature Determination

As previously described, feature sets or subsets may include respiratory mechanics based features. In some embodiments, these features may be determined automatically by a processor of a detector 100. In this regard, an automated determination of resistance R and compliance C values for the feature sets as previously described may be calculated by a multiple linear regression method.

The basis for such an algorithm for processing by the detector can rely on the application of multiple linear regression (MLR) of numerical data to a model of the patient-ventilator system. Multiple linear regression extends simple linear regression and is used to describe the relationship between a single response variable with a set of two or more explanatory variables. The relationship is linear and can be written in its basic form as $$Y_i = \beta_0 + \beta_1 x_{i,1} + \beta_2 x_{i,2} + \ldots + \beta_k x_{i,k} + \epsilon_i$$

where the random errors $\epsilon_i$, i=1, 2, . . . , n, are normally distributed random variables with zero mean and constant variance $\sigma^2$.

The patient-ventilator system can be modeled as a single compartment such that the total driving pressure is the sum of the elastic and resistive properties of the system. This can be described by a first order differential equation $$P_{tot} = R\dot{V}(t) + \frac{V(t)}{C} + P_0$$

where $P_{tot}$ is the driving pressure, $\dot{V}$ is the flow through the airways, V is the volume displaced, R is the airway resistance, C is the compliance of the respiratory system, and $P_0$ is the pressure at end-expiration which is the sum of the applied external PEEP and internal PEEP of the patient. By defining the driving pressure as the single response variable and flow and volume as the explanatory variables a processor can apply MLR to the measured data to determine the parameters R and C.

The noise in the system is predominantly random produced by turbulent flow and the ventilator turbine. The latter also produces deterministic and cyclostationary components that may influence the outcome of the model. However within the frequency range of interest (e.g., <10 Hz) they are considered to be relatively insignificant. Thus the error in the model, $\epsilon$, is a good approximation for most of the system noise.

Patient muscle effort, however, is an example of a non-random noise source that may have significant implications for the accuracy of the model. In a spontaneously breathing patient using a ventilator the driving pressure at any time is generated by both the ventilator ($P_v$) and the patient's respiratory muscles ($P_{mus}$):

$$P_{tot} = P_v + P_{mus}$$

Because $P_{mus}$ may not be measured directly without using an esophageal balloon catheter, it is difficult to accurately determine the mechanical parameters non-invasively while the patient's muscles are activated. Predominantly this is a concern during inspiration when the diaphragm and accessory muscles contract. Fitting flow and volume data to ventilator pressure data during inspiration without consideration of muscle activity would underestimate resistance and overestimate compliance:

$$P_v = R\dot{V}(t) + \frac{V(t)}{C} + P_0$$

This approach, which may be implemented by a processor in an MLR process, may allow the exclusion of influences from patient effort that would otherwise impede the accuracy of R and C.

Another example of non-random system noise is cardiogenic oscillation appearing at heart-rate bandwidth (1-2 Hz). Typically, cardiogenic oscillation produces low amplitude signals relative to the ventilated patient pressure and flow, such that it has limited effect on the model.

For these processes, differentiation between inspiration and expiration may be based on the state machine described in more detail herein that includes four states: Provisional inspiration (PI), Confirmed Inspiration (CI), Provisional Expiration (PE), Confirmed Expiration (CE). Thus, Expiratory data may be considered as that occurring from the start of a Provisional Expiration preceding a Confirmed Expiration, and up to but not including the start of the next Provisional inspiration preceding a Confirmed Inspiration.

Data used for the regression in each breath may include the beginning of expiration up to the point when approximately 85-95% (or more preferably 90%) of the tidal volume had been expired. Thus, in some embodiments only a portion (e.g., an expiratory portion) of a breathing cycle (e.g., the pressure, flow and volume measures attributable or corresponding with the expiratory portion), may be evaluated from an initial time of expiration up to a time when a desired limit (e.g., a range of 85-90 percent) of expired tidal volume is reached. A reason for this may be to optimally capture the dynamic behavior in the data. The intention of fitting the data to this model is to describe the dynamics of the passive system subjected to the pressure source. Thus, the calculations may exclude data that could be associated with patient respiratory muscle activity. Where slow flow occurs at end-expiration accompanying minimal change in pressure, the increased signal to noise ratio has the potential to introduce inaccuracy in the parameter estimation, and so this portion of the data may be omitted from the computation.

The desire for a good fit is to achieve an expiratory breath without expiratory effort or other spurious artefacts, such that the flow waveform follows an exponential decay. Thus, it may be desirable to preclude artefactual breaths from involvement with the fitting algorithm. Thus, in some embodiments, an accuracy assessment of the determination of resistance and compliance may be implemented. One way to accomplish this may be to implement a median filter, such as one with a width of about 15, such that the median values of the fitted mechanics parameters from the last number breaths (e.g., about 15) can be taken to represent the expiratory breaths with more regular exponential decay. Also a coefficient of determination $R^2$ value from the statistical fit may be used as a criterion to eliminate poorly fitted breaths. For example, a threshold of about 0.8 may be used. Thus, in such an example, a processor of an apparatus may determine accuracy, such as by determining the coefficient of determination $R^2$ value for each MLR determination of compliance and resistance values and comparing the value against with an accuracy threshold, so that certain determinations of resistance and compliance may be disregarded (e.g., determinations where the coefficient does not equal or exceed the threshold).

While the aforementioned determination of resistance and compliance values may be implemented as part of the asynchrony detection methodologies discussed herein, they may also be determined and recorded for other purposes. Thus, a processing device or respiratory treatment apparatus of the present technology may calculate these values and record this data over time, such as on a breath-by-breath basis. The values may even be averaged over a number of breaths or over a desired time period (e.g., an hour or a treatment session) or a number of treatment sessions with a respiratory treatment apparatus. The values may be output (e.g., to another processing apparatus, a display and/or memory store) so that trends in the resistance and compliance values may be evaluated. In addition to the control implementations discussed herein, the values may even serve as additional bases for making automated adjustments to the control parameters of a respiratory treatment apparatus. For example, they may be utilized for automated or manual titration of pressure settings (e.g., pressure support (PS) and/or PEEP) of a respiratory treatment device for treatment of the patient. In this regard, they may serve as a basis for an automated algorithm that makes determines, changes and/or sets a control parameter of a positive end expiratory pressure (PEEP) and/or pressure support of a respiratory treatment apparatus.

In an example of such an embodiment, automated titration of PEEP control parameters may be implemented with the aforementioned estimation of respiratory mechanics, such as the compliance value. Compliance represents the gradient of the pressure-volume (PV) curve which is used commonly in clinical practice as a diagnostic aide. The PV curve is sigmoid in shape where low compliance occurs at the lower and upper extremities of the curve beyond the lower and upper inflection points. Optimal ventilation strategy, in particular the titration of PEEP and PS, would exploit the mid-linear portion of the PV curve.

In an example embodiment of the automatic titration of PEEP, a processor of a titration apparatus (e.g., an autotitrating respiratory treatment apparatus) may be implemented with a PEEP titration methodology as follows:

1. Without additionally using pressure support PS, a PEEP control parameter of a respiratory treatment apparatus is initialized at a higher value (e.g., 10-15 cmH$_2$O) to ensure maximal recruitment of alveoli.

Figure 19:
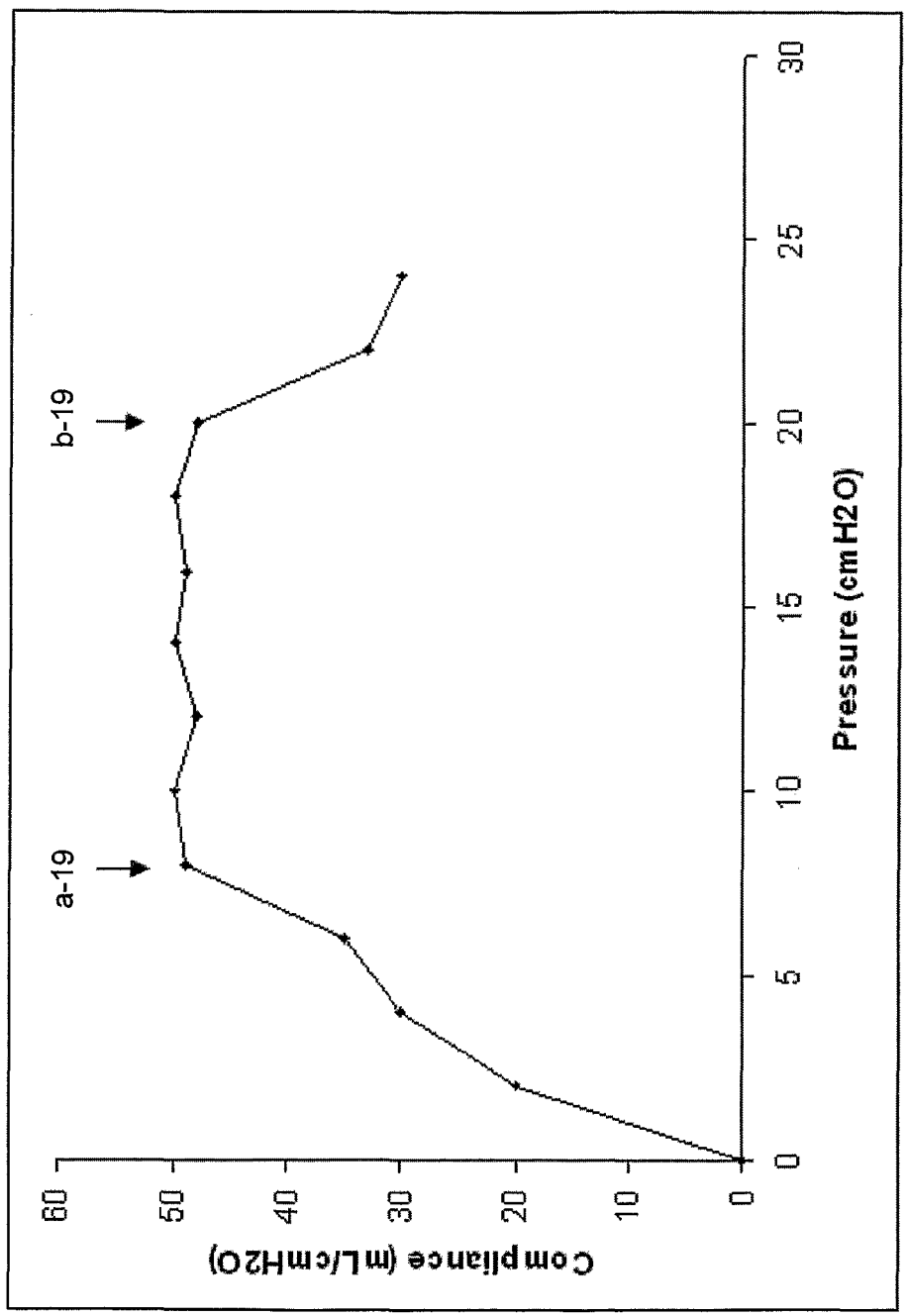
FIG. 19 is a graph illustrating example titration methods based on determined respiratory mechanics values of the present technology.

2. The PEEP parameter is then decremented (e.g., breath-by-breath), and the corresponding compliance value is determined or monitored at each step with respect to its associated PEEP parameter of the breath or breaths from which the compliance is determined.
3. Using the resulting trend in compliance, the inflection point that indicates a significant reduction is located.
4. An appropriate PEEP parameter is chosen, for example, as the pressure level one increment higher than the pressure level corresponding to the inflection point. This inflection point is illustrated in the graph of FIG. 19 at arrow a-19.

In an example embodiment of an automatic titration of a maximum limit for pressure support PS, a processor of a titration apparatus (e.g., an autotitrating respiratory treatment apparatus) may also be implemented with a methodology, which may optionally follow the preceding PEEP titration methodology, as follows:
1. Without additionally using PS, the PEEP control parameter is initialized at a higher value (e.g., 10-15 cmH2O) to ensure maximal recruitment of alveoli.
2. The PEEP parameter is then incremented (e.g., breath by breath) until a significant drop is observed in compliance which is monitored at each step.
3. An appropriate maximum PS limit is chosen, such as the pressure level one increment lower than that corresponding to the inflection point. This is also illustrated in FIG. 19 at inflection point shown at arrow b-19.

Example Technological Embodiments

In some embodiments of the present technology, automated methods are implemented to detect not only a general occurrence of a ventilator-patient asynchrony event but different types of asynchrony events such as two or more of the illustrated asynchrony events of FIGS. 3-9. This detection of a plurality of distinct asynchrony events may be implemented by automated processing of the data from a flow signal and/or a pressure signal measured by suitable sensors during delivery of ventilatory assistance by a ventilator or other respiratory treatment device. For example, the detection of the distinct events may be based on a pre-determination of a set of detection variables including, for example, respiratory rate based features, volume based features, respiratory mechanics based features, expiratory flow morphology based features, power based power based features, or other features referred to herein etc., that are derivable with pressure and/or flow data. For example, such detection variables may be any one or more of the following example detection variables: RR breath, RR ratio, IE ratio, $Vol_I$, $Vol_E$, breathLeak, Vol ratio, $PEEPi_i$, $R_i$, $C_i$, $Tau_i$, $PEEPi_e$, $R_e$, $C_e$, $Tau_e$, InterpMinima, InterpMinima-⅔, PW linear approx power, PW vol deviation, PW dist flow maxmin, PW distance ratio, power $\Phi_{int}$, power ⅔$\Phi_{int}$, power $\Phi_{pw}$, integral $\Phi_{pw}$, gradient-a, gradient-b, amplitude p-t $\Phi_{pw}$, duration p-t $\Phi_{pw}$, volIE, zxUpCount, maxFlowIE, heightIE, durIE, rangeP-P, durP-P, ampRatio, volRatio, durRatio, locationIE, peaksCount, timeElapsed, falseExpVol, and/or expRatio.

The set of variables may be chosen according to an optional feature subset selection process as previously described. The chosen subset of detection variables may be compared to one or more thresholds or threshold functions to detect the event conditions with the variables. The thresholds for chosen variables may be determined or optimized by a suitable automated classification criteria according to empirical/clinician classification of observed events such as those discussed herein. In addition, the evaluation of variables and detection of the event conditions may be further based on an automated respiratory phase detection (e.g., detection of inspiration or expiration phases, such as with an implemented version of the state diagram shown above).

The automated processing to detect the different types of asynchrony by evaluating the set of variables may be performed by a processing apparatus (e.g., a programmed general purpose computer having memory and one or more processors or a specific purpose computer) with previously recorded flow and/or pressure data or by a ventilator during treatment while such measures are being determined. Thus, the methodologies may be implemented by one or more processors with software or firmware and/or with application specific integrated chips that embody the detection methodologies illustrated herein. In some embodiments of the technology, adjustments to respiratory treatment by a ventilator may be automated according to the detected events. For example, a controlled treatment response of a ventilator may be modified according to which asynchrony type is detected such that one type of event may generate a different automatic ventilator or respiratory treatment response. Furthermore, the detected events may be recorded or scored. Thus, such an apparatus may generate a report of occurrence details of the different events such as how many have occurred, when they have occurred etc. These details may optionally be displayed in association with the values of the detection variables or set of detection variables and other flow or pressure data.

For example, in one embodiment, a plurality of distinct asynchrony events or an asynchrony event may be detected by a processing apparatus or respiratory treatment apparatus from data representing a flow and/or pressure measurements taken during respiratory treatment with a cycling respiratory treatment apparatus. In one such embodiment, a set of detection variables may include one or more of measures of PW linear approx power, PW dist flow maxmin, PW vol deviation, $Tau_t$ and PW distance ratio determined by a processor of the processing apparatus or respiratory treatment apparatus. These variables may then be compared to their associated predetermined thresholds by the processing apparatus to detect whether or not an expiratory ineffective effort asynchrony event has occurred or not. The processing apparatus or respiratory treatment apparatus may further detect or score other types of asynchrony events such as one or more of Post-triggering Effort, Double Triggering, Autotriggering, Late Triggering, Early Cycling and/or Late Cycling.

Optionally, in some embodiments, the detection of these asynchrony events may be excluded (i.e., not scored) by the apparatus upon automated detection of artifacts such as coughs, swallowing, etc. The determination of such events is illustrated in International Patent Publication No. WO 2006/079152, the entire disclosure of which is incorporated herein by reference.

In some embodiments of the technology, an apparatus is configured for automated detection of two or more distinct types of asynchrony events from data representing flow and/or pressure measurements taken during pressure treatment with a cycling respiratory treatment device or ventilator.

In some embodiments of the technology, an apparatus is configured for automated detection of an expiratory ineffective effort asynchrony event based on data representing flow and/or pressure measurements taken during pressure treatment with a cycling respiratory treatment device or ventilator.

In some embodiments of the technology, an apparatus is configured for automated detection of an expiratory ineffective effort asynchrony event based on data representing flow and/or pressure measurements taken during pressure treatment with a cycling respiratory treatment device or ventilator, where the detection involves an analysis of two or more calculated features representing respiratory mechanics based features and/or expiratory flow morphology based features, such as, PW linear approx power, PW dist flow maxmin, PW vol deviation, $Tau_i$ and PW distance ratio. For example, the analysis may be a comparison of the calculated features with a set of thresholds or threshold functions.

In some embodiments of the technology, an apparatus is configured for automated detection of a post-triggering effort asynchrony event based on data representing flow and/or pressure measurements taken during pressure treatment with a cycling respiratory treatment device or ventilator.

In some embodiments of the technology, an apparatus is configured for automated detection of a double triggering asynchrony event based on data representing flow and/or pressure measurements taken during pressure treatment with a cycling respiratory treatment device or ventilator.

In some embodiments of the technology, an apparatus is configured for automated detection of an autotriggering asynchrony event based on data representing flow and/or pressure measurements taken during pressure treatment with a cycling respiratory treatment device or ventilator.

In some embodiments of the technology, an apparatus is configured for automated detection of a late triggering asynchrony event from based on representing flow and/or pressure measurements taken during pressure treatment with a cycling respiratory treatment device or ventilator.

In some embodiments of the technology, an apparatus is configured for automated detection of an early cycling asynchrony event from based on representing flow and/or pressure measurements taken during pressure treatment with a cycling respiratory treatment device or ventilator.

In some embodiments of the technology, an apparatus is configured for automated detection of a late cycling asynchrony event based on data representing flow and/or pressure measurements taken during pressure treatment with a cycling respiratory treatment device or ventilator.

Any one, some or all of the detected asynchrony events may serve as a metric for non-invasively and simply determining the quality of patient-ventilator interaction based on processing of flow or pressure measurements. Thus, other measurement devices or equipment does not necessarily need to be utilized.

Although in some embodiments implemented thresholds may be optimized from empirical or clinical observation of data from many patients, asynchrony detection utilizing any of the previous mentioned features may be optimized for a particular patient through clinical observation of flow and/pressure data from the particular patient and by utilizing automated feature selection and automated classification of the selected features for that particular patient by the methods previously mentioned. Thus, a detection or treatment apparatus may be tuned or programmed for an individual subject according to the results of an automated selection of features and thresholds determination made by a separate tuning apparatus or computer that is programmed to perform the feature subset selection and threshold determination. Optionally, these methodologies may also be integrated within the programming of a ventilator or respiratory treatment device.

An apparatus with the implemented detection of asynchrony events can serve as a tool to permit understanding of the mechanisms of asynchrony by relating influence of physiological parameters on particular asynchronies.

The apparatus may also serve as a tool for predicting asynchronies in patient-ventilator use for particular subject. Thus, prognosis for ventilator therapy for that subject may be assessed with respect to compliance to therapy, hospitalization stay, weaning success, mortality, onset of COPD exacerbation, sleep quality etc.

The automated detection of one or more of the different types of asynchrony events in a ventilator or cycling respiratory treatment device can serve as a control feedback for servo-titration of the device during patient treatment (e.g., smart therapy algorithms).

Other embodiments and modifications thereof will be apparent from consideration of all of the details of the present disclosure.

Example Respiratory Treatment Apparatus Embodiment

Figure 11:
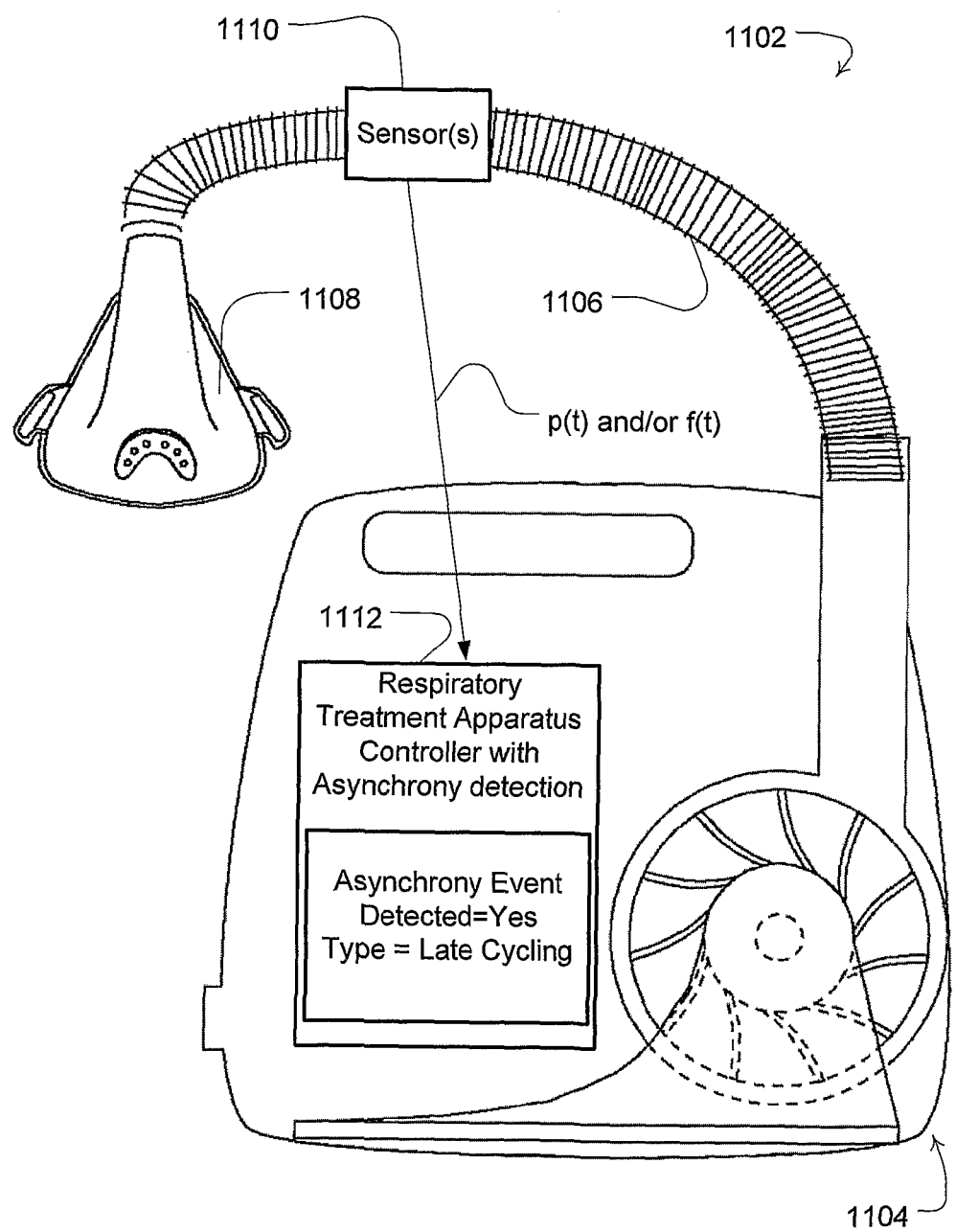
FIG. 11 is an example respiratory treatment apparatus with an asynchrony detection controller.

In reference to FIG. 11, the present asynchrony detection technology may be implemented with a respiratory treatment apparatus 1102, such as a ventilator or other respiratory treatment apparatus that synchronizes treatment operations with patient respiration. Such an apparatus may include a flow generator such as a servo-controlled blower 1104. The blower 1104 can typically include an air inlet and impeller driven by a motor (not shown).

The respiratory treatment apparatus 1102 will also typically include a patient interface such as an air delivery conduit 1106 and a mask 1108 or endrotracheal tube (not shown) to carry a flow of air or breathable gas to and/or from a patient.

The apparatus 1102 also may include sensors 1110, such as a pressure sensor and/or flow sensor. In such an embodiment, the pressure sensor, such as a pressure transducer, may measure the pressure generated by the blower 1104 and generate a pressure signal p(t) indicative of the measurements of pressure, such as the pressure at the airway. Similarly, the flow sensor generates a signal representative of the patient's respiratory flow. For example, flow proximate to the patient interface or a sense tube (not shown) may be measured using a pneumotachograph and differential pressure transducer or similar device such as one employing a bundle of tubes or ducts to derive a flow signal f(t). This flow signal may optionally be adjusted to compensate for offset and leak. Other sensors may be utilized to generate data indicative of flow or pressure for the purposes of the methodologies of the apparatus. For example, in some embodiments it may also include a transdiaphragmatic pressure sensor to generate a signal representative of transdiaphragmatic pressure. Similarly, it may also optionally include a sensor(s) suitable for generating a signal(s) representative of Pleural pressure and/or abdominal pressure.

Based on the sensor signals, such as the flow f(t) and/or pressure p(t) signals, a controller 1112 may generate blower control signals. For example, the controller may generate a desired pressure set point and servo-control the speed of the blower to meet the set point by comparing the set point with the measured condition of the pressure sensor. Thus, the controller 1112 may make controlled changes to the pressure delivered to the patient interface by the blower 1104. Typically, such settings may be made to synchronize a treatment with patient respiration or to support the patient's respiration and may be made in conjunction with a detection of a state of a patient respiration such as by analysis of the flow signals in conjunction with control parameters such as trigger and cycling thresholds. Optionally, changes to pressure may be implemented by controlling an exhaust with a mechanical release valve (not shown) to increase or decrease the exhaust while maintaining a relatively constant blower speed. Similarly, based on flow f(t) and/or pressure p(t) signals, a controller 1112 may implement the present asynchrony event detection methodologies described in more detail herein.

Thus, the controller 1112 may include one or more processors programmed to implement particular methodologies or algorithms described in more detail herein. To this end, the controller may include integrated chips, a memory and/or other control instruction, data or information storage medium. For example, programmed instructions encompassing such a control methodology may be coded on integrated chips in the memory of the device. Such instructions may also or alternatively be loaded as software or firmware using an appropriate data storage medium.

In some such embodiments, the controller may detect or score asynchrony events and modify pressure control parameters for the respiratory treatment based on the detection or scoring of such asynchrony events. For example, if one or more of ineffective inspiratory effort asynchrony events have been detected, the controller may automatically reduce (e.g., step down) a triggering threshold used by the controller to detect patient inspiration and initiate control of an inspiratory pressure level. Further step changes may also be made upon continued detection of the asynchrony events. Optionally, in response to the detection of a number of such asynchrony events, the controller or processor may generate an output message for a clinician to indicate that a change to the trigger threshold setting should be manually made or has been automatically made. Similarly, detection of late triggering asynchrony events may serve to control step changes or messages concerning the trigger threshold of the respiratory treatment apparatus. In such as case, the step change made or suggested in response to a late triggering may be smaller than the step change associated with the detection of ineffective efforts asynchrony events.

By way of further example, detection of autotriggering asynchrony events may serve to control one or more step changes or messages to increase the trigger threshold of the respiratory treatment apparatus. Through controlling step increases and decreases in the triggering threshold based on the different asynchrony events to reduce the counts of these events, the trigger threshold may be servo controlled to an optimum setting.

In a similar fashion, adjustments to the respiratory treatment apparatus' cycling threshold may be made or suggested by the controller or processor upon detection of late cycling and/or early cycling events to reduce these events and thereby optimize the setting for the cycling threshold.

Other changes to the control parameters of the respiratory treatment apparatus may also be made or suggested in accordance with the detection of the asynchrony events.

Example Controller/Processing Apparatus Architecture

Figure 12:
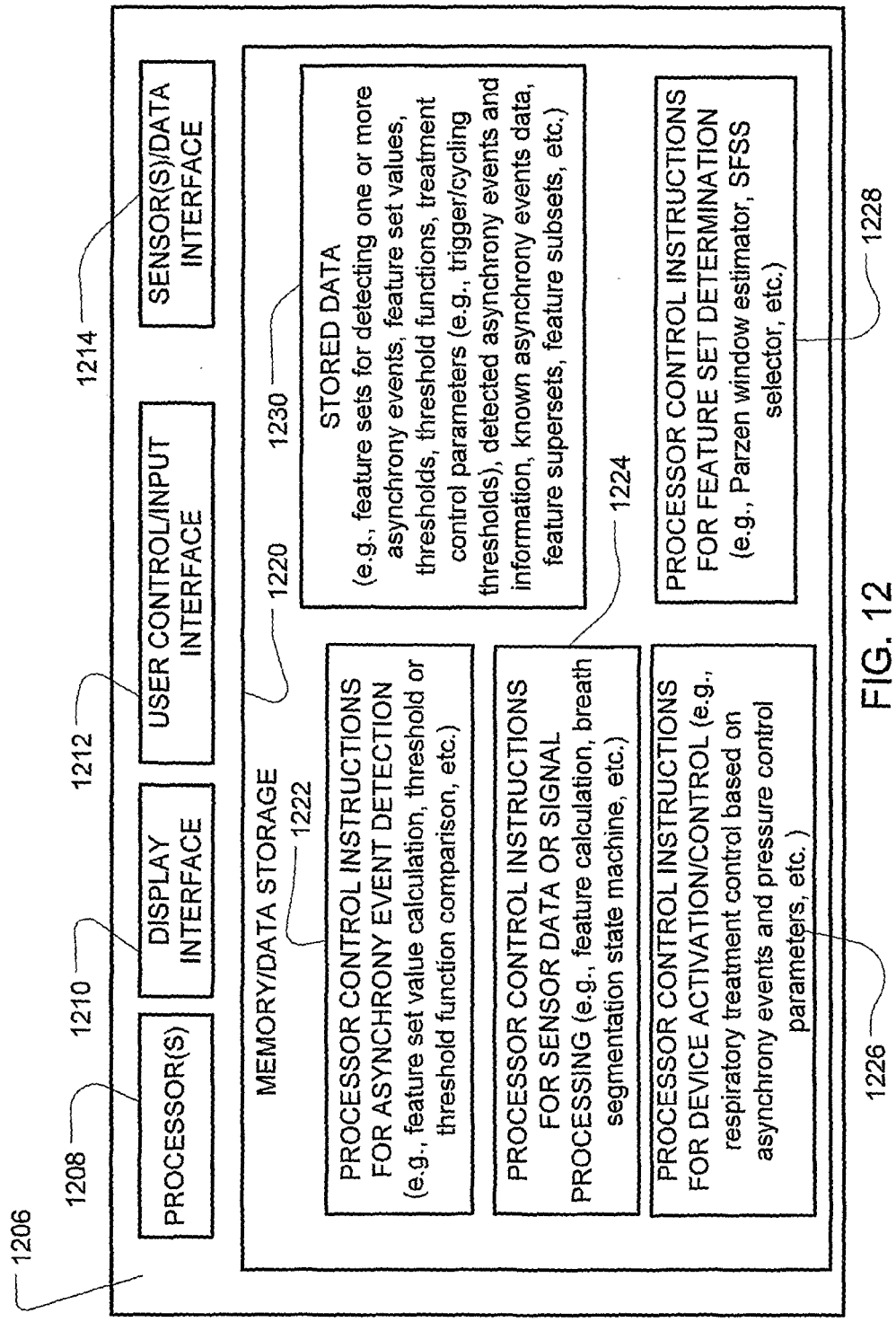
FIG. 12 is a block diagram illustrating suitable components that may be implemented as a processing apparatus or controller for embodiments of the present technology.

An example system architecture of a processing apparatus (e.g., computer or controller 1112) is illustrated in the block diagram of FIG. 12. The system architecture may serve as a respiratory treatment apparatus controller with asynchrony detection or more simply as a stand alone asynchrony detector such as a special purpose computer. In the illustration, the detection device 1206 may be implemented by a general purpose computer with one or more programmable processors 1208. The device may also include a display interface 1210 to output data from the detection methodologies as previously discussed (e.g., asynchrony events and information, etc.), results or graphs as described herein to a display such as on a monitor or LCD panel. A user control/input interface 1212, for example, for a keyboard, touch panel, control buttons, mouse etc. may also be included for inputting data, or otherwise activating or operating the methodologies described herein. The device may also include a sensor or data interface 1214, such as a bus, for receiving/transmitting data such as programming instructions, flow data, pressure data, asynchrony data, feature set calculation algorithms, feature subset selection algorithms, feature set values and other output or input of the previously described methodologies.

The device also includes memory/data storage components 1220 containing control instructions and data of the aforementioned methodologies and algorithms. At 1222, these may also include stored processor control instructions for asynchrony event detection as discussed in more detail herein. For example, this may include feature set value calculation instructions and threshold or threshold function comparison instructions. For example, at 1224, they may include stored processor control instructions for flow and pressure signals processing such as feature calculation and breath segmentation. At 1226, they may also include processor control instructions for device activation control such as respiratory treatment control parameters, ventilation control parameters or pressure treatment synchronization methodologies. This may also include, for example, pressure control adjustment based on detected asynchrony events, etc. Optionally or alternatively, at 1228, they may also include processor control instructions for feature set determination such as instructions for a Parzen window estimator, SFSS selector, etc. Finally, they may also include stored data at 1230 for these methodologies such as flow data, pressure data, breath segmentation data, features sets for detecting one or more asynchrony events, features set values, thresholds, threshold functions, detected asynchrony events and related information, known asynchrony events data, feature subsets, features supersets, reports and graphs, etc.

In some embodiments, some or all of the processor control instructions and data for controlling the above described methodologies may be contained in a computer readable recording medium as software for use by a general purpose computer so that the general purpose computer may serve as a specific purpose computer according to any of the methodologies discussed herein upon loading the software into the general purpose computer.

In the foregoing description and in the accompanying drawings, specific terminology, equations and drawing symbols are set forth to provide a thorough understanding of the present technology. In some instances, the terminology and symbols may imply specific details that are not required to practice the technology. Moreover, although the technology herein has been described with reference to particular embodiments, it is to be understood that these embodiments are merely illustrative of the principles and applications of the technology. It is therefore to be understood that numerous modifications may be made to the illustrative embodiments and that other arrangements may be devised without departing from the spirit and scope of the technology. For example, in some detector embodiments, in addition to flow and/or pressure data, feature sets may be also be based on data from transdiaphragmatic pressure signals.

The invention claimed is:

1. An apparatus for detection of asynchrony between a synchronized respiratory treatment and a respiratory cycle, the apparatus comprising:
   a memory containing data representing a feature set of detection values derived from signals of at least one sensor coupled with a respiratory treatment apparatus, in which the feature set of detection values includes a plurality of features as respective individual parameter detection variables derived from a pattern of flow indicated by the signals; and a controller of the respiratory treatment apparatus, wherein the controller is configured to access the data, and to control:

a comparison of the individual parameter detection variables respectively of the plurality of features of the data of the feature set of detection values respectively with a set of associated thresholds for the individual parameter detection variables of the memory, the set of associated thresholds for the individual parameter detection variables being from other than the signals;

a determination of an occurrence and type of an asynchrony event between the respiratory treatment apparatus and a patient respiratory cycle based on the comparison, wherein the determination of the occurrence and type of the asynchrony event identifies time of occurrence of a distinct asynchrony event of a plurality of distinct asynchrony events comprising at least two distinct events of (a) a post-triggering effort event, (b) a double triggering event, (c) a late triggering event, (d) an auto triggering event, (e) an early cycling event, and (f) a late cycling event; and a generation of an output representing the occurrence of the asynchrony event, in which the controller is configured to control the respiratory treatment apparatus based on the determination of the occurrence and type of the asynchrony event.

2. The apparatus of claim 1 further comprising a patient interface to carry a flow of breathable gas to a patient;

a flow generator coupled with the patient interface to generate a flow of the breathable gas through the patient interface;

a transducer to provide a signal indicative of patient flow through the patient interface;

wherein the controller is configured to control the flow generator, detect a respiratory cycle with the signal of the flow sensor and generate flow generator control signals for producing the respiratory treatment.

3. The apparatus of claim 2 wherein the feature set of detection values comprises a respiratory rate based feature as one of the individual parameter detection variables.

4. The apparatus of claim 2 wherein the feature set of detection values comprises a respiratory volume based feature as one of the individual parameter detection variables.

5. The apparatus of claim 2 wherein the feature set of detection values comprises a respiratory mechanics based feature as one of the individual parameter detection variables.

6. The apparatus of claim 5 wherein the controller is configured to control determining resistance and compliance values based on measures of pressure, flow and volume.

7. The apparatus of claim 6 wherein the controller is configured to control multiple linear regression processing of the measure of pressure, flow and volume.

8. The apparatus of claim 7 wherein the controller is further configured to control an assessment of accuracy of the determined resistance and compliance values.

9. The apparatus of claim 8 wherein the assessment of accuracy comprises calculating a coefficient of determination and comparing the coefficient of determination to a threshold.

10. The apparatus of claim 7 wherein the determining of resistance and compliance values is based on the measures taken from a portion of a detected breathing cycle.

11. The apparatus of claim 10 wherein the portion is an expiratory portion.

12. The apparatus of claim 11 wherein the portion is an initial part of expiration during which a percentage of tidal volume is expired.

13. The apparatus of claim 12 wherein the percentage is in a range of about 85 to 90 percent.

14. The apparatus of claim 2 wherein the feature set of detection values comprises an expiratory flow morphology based feature as one of the individual parameter detection variables.

15. The apparatus of claim 2 wherein the asynchrony event comprises an expiratory ineffective effort event.

16. The apparatus of claim 15 wherein the feature set of detection values comprises as the individual parameter detection variables (a) a power of a piecewise bilinear approximation of a remainder of expiration after a location of a maximum expiratory flow, (b) a distance between a maximum and minimum values of a moving average expiratory flow, (c) an integral of a rectified and de-trended moving average of expiratory flow, (d) an inspiratory time constant, and (e) a fraction of said distance and a peak expiratory flow.

17. The apparatus of claim 15 wherein the feature set comprises a determined volume of gas moved during the ineffective effort event.

18. The apparatus of claim 2 wherein the asynchrony event comprises the post-triggering effort event.

19. The apparatus of claim 2 wherein the asynchrony event comprises the double triggering event.

20. The apparatus of claim 19 wherein the feature set comprises a maxima count and an elapsed time between maxima.

21. The apparatus of claim 2 wherein the asynchrony event comprises the autotriggering event.

22. The apparatus of claim 2 wherein the asynchrony event comprises the late triggering event.

23. The apparatus of claim 2 wherein the asynchrony event comprises the early cycling event.

24. The apparatus of claim 2 wherein the asynchrony event comprises the late cycling event.

25. The apparatus of claim 2 wherein the asynchrony event comprises an inspiratory ineffective effort event.

26. The apparatus of claim 2 wherein the controller is configured to automatically change a control parameter for delivery of the respiratory treatment based on the occurrence of the asynchrony event.

27. The apparatus of claim 26 wherein the control parameter comprises a trigger threshold.

28. The method of claim 26 wherein the control parameter comprises a cycling threshold.

29. The apparatus of claim 2 wherein the respiratory treatment apparatus comprises a ventilator.

30. The apparatus of claim 1 wherein the controller is further configured to control selecting the feature set such that the feature set comprises a subset of a superset of features, wherein the selecting comprises evaluating values of the superset for known asynchronous events occurring in data of a plurality of breaths established with a plurality of respiratory treatment apparatus.

31. The apparatus of claim 30 wherein the evaluating comprises calculating posterior-probabilities with values of the superset by Parzen-window estimation, wherein groups of values of the superset are selected by iteratively including and removing values.

32. A system for detection of asynchrony between a synchronized respiratory treatment and a respiratory cycle comprising:

a controller configured to control a respiratory treatment apparatus and to process data derived from one or more pressure transducer signals from use of the respiratory treatment apparatus, the controller being configured to (a) compare respective individual parameter detection variables, in which a feature set of detection values calculated from the data includes a plurality of features as the respective individual parameter detection variables derived from a pattern of flow indicated by the signals, with a set of associated thresholds for the individual parameter detection variables, the set of associated thresholds for the individual parameter detection variables being from other than the signals, and (b) determine an occurrence and type of an asynchrony event between the respiratory treatment apparatus and a patient respiratory cycle based on the comparison, wherein the determination of the occurrence and type of the asynchrony event identifies time of occurrence of a distinct asynchrony event of a plurality of distinct asynchrony events comprising at least two distinct events of (a) a post-triggering effort event, (b) a double triggering event, (c) a late triggering event, (d) an auto triggering event, (e) an early cycling event, and (f) a late cycling event, in which the controller is configured to control the respiratory treatment apparatus based on the determination of the occurrence and type of the asynchrony event.

33. The system of claim 32, wherein the controller is configured to select the feature set such that the feature set comprises a subset of a superset of features, wherein the feature set is selected by evaluating values of the superset for known asynchronous events occurring in data of a plurality of breaths established with a plurality of respiratory treatment apparatus.

34. The system of claim 33 wherein the controller is further configured to calculate the detection values of the feature set with the data derived from signals of at least one sensor coupled to the respiratory treatment apparatus.

35. The system of claim 34 wherein the feature set of detection values comprises two or more of features of a group of features consisting of (a) a respiratory rate based feature; (b) a respiratory volume based feature; (b) a respiratory mechanics based feature; and (d) an expiratory flow morphology based feature.

36. The system of claim 32 wherein the at least two distinct events includes an expiratory ineffective effort event.

37. The system of claim 32 further comprising:
an interface to carry a flow of breathable gas;
a flow generator, coupled with the interface, that generates the breathable gas; and
a flow sensor for generating the pressure transducer signals;
wherein the controller is further configured to control the flow generator to provide a synchronized respiratory treatment.

38. The system of claim 37 wherein the synchronized respiratory treatment is respiratory support ventilation.

39. A non-transitory information-bearing medium having processor-readable information thereon, the processor-readable information to control a respiratory treatment apparatus and an apparatus for detection of asynchrony between a synchronized respiratory treatment and a respiratory cycle, the processor-readable information comprising control instructions to:

access detection values of a feature set with data derived from signals of at least one sensor coupled with the respiratory treatment apparatus, in which the feature set of detection values includes a plurality of features as respective individual parameter detection variables derived from a pattern of flow indicated by the signals;

compare the individual parameter detection variables respectively of the feature set of detection values with a set of associated thresholds for the individual parameter detection variables, the set of associated thresholds for the individual parameter detection variables being from other than the signals;

determine an occurrence and type of an asynchrony event between the respiratory treatment apparatus and a patient respiratory cycle based on the comparison;

wherein the determination of the occurrence and type of the asynchrony event identifies time of occurrence of a distinct asynchrony event of a plurality of distinct asynchrony events comprising at least two distinct events of (a) a post-triggering effort event, (b) a double triggering event, (c) a late triggering event, (d) an auto triggering event, (e) an early cycling event, and (f) a late cycling event, in which the apparatus for detection of asynchrony is configured to control the respiratory treatment apparatus based on the determination of the occurrence and type of the asynchrony event.

* * * * *